(12) United States Patent
Chew et al.

(10) Patent No.: US 9,808,374 B2
(45) Date of Patent: Nov. 7, 2017

(54) OCULAR DRAINAGE DEVICE AND METHOD OF MANUFACTURING THEREOF

(71) Applicants: NATIONAL UNIVERSITY OF SINGAPORE, Singapore (SG); NATIONAL UNIVERSITY HOSPITAL (SINGAPORE) PTE LTD, Singapore (SG)

(72) Inventors: Tec Kuan Paul Chew, Singapore (SG); Keith Barton, Singapore (SG); Eugene Khor, Singapore (SG); Chelvin Cheryl Agnes Sng, Singapore (SG)

(73) Assignees: NATIONAL UNIVERSITY OF SINGAPORE, Singapore (SG); NATIONAL UNIVERSITY HOSPITAL (SINGAPORE) PTE LTD, Singapore (SG)

( * ) Notice: Subject to any disclaimer, the term of this patent is extended or adjusted under 35 U.S.C. 154(b) by 0 days.

(21) Appl. No.: 15/102,267

(22) PCT Filed: Feb. 24, 2015

(86) PCT No.: PCT/SG2015/050026
§ 371 (c)(1),
(2) Date: Jun. 6, 2016

(87) PCT Pub. No.: WO2015/126332
PCT Pub. Date: Aug. 27, 2015

(65) Prior Publication Data
US 2017/0020730 A1    Jan. 26, 2017

Related U.S. Application Data

(60) Provisional application No. 61/943,922, filed on Feb. 24, 2014, provisional application No. 61/943,930, filed on Feb. 24, 2014.

(51) Int. Cl.
*A61M 5/00* (2006.01)
*A61F 9/007* (2006.01)
(Continued)

(52) U.S. Cl.
CPC ...... *A61F 9/00781* (2013.01); *B29C 45/1671* (2013.01); *A61F 2240/001* (2013.01); *B29K 2021/00* (2013.01); *B29L 2031/753* (2013.01)

(58) Field of Classification Search
CPC .......... A61F 9/00781; A61F 2240/001; B29C 45/1671; B29K 2021/00; B29L 2031/753
(Continued)

(56) References Cited

U.S. PATENT DOCUMENTS 5,171,213 A    12/1992    Price, Jr.
5,300,020 A     4/1994    L'Esperance, Jr.
(Continued)

FOREIGN PATENT DOCUMENTS

CN    1864654 A    11/2006
DE    69513530 T    5/2000
(Continued)

OTHER PUBLICATIONS

International Search Report and Written Opinion of PCT/SG2015/050026.
(Continued)

*Primary Examiner* — Philip R Wiest
(74) *Attorney, Agent, or Firm* — Joseph G. Chu; JCIP

(57) ABSTRACT

Aspects of the present disclosure are directed to an ocular drainage device that includes a stability system. The stability system includes a plate, and can further include a material comprising collagen covering at least a portion of a top surface of the plate, and/or a viscoelastic substance covering at least a portion of the plate's top surface. The plate is formed of a flexible material and includes a tube retaining (Continued)

structure integrally formed therewith, wherein the tube retaining structure is configured to hold a tube that is at least partially surrounded by the tube retaining structure to the plate when the tube is moved. The tube retaining structure can include a low profile ridge, and/or a channel having an undercut or horseshoe shape. The plate has at least one plate channel, including a plate channel configured for carrying the tube. The plate can further include a reservoir.

20 Claims, 14 Drawing Sheets

(51) Int. Cl.
 *B29C 45/16* (2006.01)
 *B29K 21/00* (2006.01)
 *B29L 31/00* (2006.01)
(58) Field of Classification Search
 USPC .............................................................. 604/9
 See application file for complete search history.

(56) References Cited

U.S. PATENT DOCUMENTS

| | | | |
|---|---|---|---|
| 5,476,445 A | 12/1995 | Baerveldt et al. | |
| 5,882,327 A | 3/1999 | Jacob | |
| 9,339,514 B2 * | 5/2016 | Bos | A61K 9/0051 |
| 2002/0156413 A1 | 10/2002 | Williams et al. | |
| 2005/0267398 A1 * | 12/2005 | Protopsaltis | A61F 9/00781 604/8 |
| 2007/0078371 A1 | 4/2007 | Brown et al. | |
| 2007/0293872 A1 * | 12/2007 | Peyman | A61F 9/00781 606/107 |
| 2010/0114006 A1 | 5/2010 | Baerveldt | |
| 2010/0241046 A1 | 9/2010 | Pinchuk et al. | |
| 2010/0249691 A1 | 9/2010 | Van Der Mooren | |
| 2012/0123316 A1 * | 5/2012 | Horvath | A61F 9/00781 604/8 |
| 2013/0184631 A1 * | 7/2013 | Pinchuk | A61F 9/00781 604/8 |

FOREIGN PATENT DOCUMENTS

| | | |
|---|---|---|
| JP | 06509732 A | 11/1994 |
| JP | 10503405 A | 3/1998 |
| JP | 2013202088 A | 10/2013 |
| WO | 9118568 A1 | 12/1991 |
| WO | 9303778 A1 | 3/1993 |
| WO | 9603944 A1 | 2/1996 |
| WO | 2004073564 A2 | 9/2004 |
| WO | 2010111528 A4 | 9/2010 |
| WO | 2013155252 A1 | 10/2013 |

OTHER PUBLICATIONS

Office Action of Chinese Patent Application No. 2015800102686 dated Apr. 25, 2017.
Search Report from European Patent Office for patent application No. 15752505.6 dated Aug. 17, 2017.

* cited by examiner

SECTION A-A

Key:

NO: No Tutopatch & No Healaflow

P & H: With Tutopatch & With Healaflow

OCULAR DRAINAGE DEVICE AND METHOD OF MANUFACTURING THEREOF

TECHNICAL FIELD

The present disclosure generally relates to the field of Ophthalmology. In particular, the present disclosure relates to implantable ocular devices including ocular drainage devices. More specifically, the present disclosure relates to a glaucoma drainage device (hereinafter referred to as 'GDD'), a method of manufacturing the GDD, and a method of implanting the GDD.

BACKGROUND

Glaucoma causes irreversible blindness if left untreated. Sixty (60) million people were diagnosed with glaucoma in 2010, eight (8) million of whom progressed to blindness. Glaucoma occurs when the intraocular pressure (IOP) in the eye increases above normal levels due to a higher inflow of aqueous fluid than outflow. While drug therapy is effective, compliance is a problem as drug therapy usually entails multi-drug regimens. For example, a study has shown that for patients undergoing drug therapy there is 50% non-compliance at 6 months of drug therapy. Trabeculectomy, which is invasive, is typically used when drug therapy fails. While trabeculectomy can be effective, it has been shown to have a 46.9% failure rate at 5 years after surgery primarily due to the formation of scar tissues.

Glaucoma drainage devices (hereinafter 'GDDs') can be used for patients refractory to drug treatment and patients who have undergone a failed trabeculectomy. There is now mounting evidence that GDDs, typically used only in the most refractory of cases, are as safe and effective as trabeculectomy in IOP control. In some cases, GDDs have been found to be more effective than trabeculectomy in IOP control.

GDDs, also known as glaucoma filtering devices or aqueous shunts, are surgical implants that permit the drainage of intraocular fluid from the interior of the eye to the exterior of the eye thereby lowering intraocular pressure. GDDs have been in use since the early 1970s and two standard designs persist. To date, no significant advances in the design of GDDs have been made.

The challenge is in improving the design of GDDs to eliminate the problems associated with presently available GDDs. For example, with respect to presently available GDDs, at 5 years after surgical implantation a conventional Baerveldt device has shown a 36% failure rate, and a conventional Ahmed device has shown a 44% failure rate. Such failure rates are due to occluded flow, inflammation, and fibrous encapsulation associated with the presently available GDDs.

Therefore, there is a need to provide a glaucoma drainage device (GDD) that avoids or at least ameliorates one or more of the disadvantages described above. The non-limiting exemplary embodiments of a GDD of the present disclosure satisfy such a need.

SUMMARY

The present disclosure relates to a glaucoma drainage device (GDD) having an improved design over presently available glaucoma drainage devices (GDDs). The improved design of the GDD of the present disclosure can allow for an improved surgical implantation technique for implanting the GDD. Additionally, the improved design of the GDD of the present disclosure can prevent complications associated with presently available GDDs. Further, the improved design of the GDD of the present disclosure can provide for improved performance in reducing intraocular pressure (IOP) to acceptable levels in comparison to presently available GDDs.

In general, the improvements and success rate associated with a GDD of the present disclosure can be dependent on the design of the GDD, the materials used to manufacture the GDD, and/or method of manufacturing the GDD.

The present disclosure also relates to a plate of a GDD, wherein the plate design can be optimized for bleb formation and/or fluid control.

The present disclosure also relates to a tube of a GDD, wherein the tube can be designed for fluid control, easier insertion at a distal end of the tube, and/or easier length correction and/or modification at a proximal end of the tube.

The present disclosure also relates to a mechanism designed to control the diameter of a tube of a GDD, wherein the mechanism can create a smaller diameter for the tube for the first four (4) to eight (8) weeks after surgical implantation. At eight (8) weeks after surgical implantation and/or beyond eight (8) weeks after surgical implantation, the diameter of the tube can increase in size to its original diameter and/or final diameter and consequently influence the rate of fluid exiting the eye.

Additionally, the present disclosure relates to a stability system or fluid flow control system, wherein the stability system can prevent complications associated with presently available GDDs. The stability system can provide additional resistance to fluid flow thereby acting as a flow restrictor to prevent hypotony immediately post-operation/post-surgical implantation. In addition, the stability system can act as a spacer that prevents sticking of the conjunctiva to the sclera flap thereby resulting in better bleb formation. The improved bleb formation can result in better long-term fluid flow control thereby ameliorating the hypertensive phase that typically occurs after one month post-operation/post-surgical implantation.

The new and unique design of a GDD of the present disclosure can utilize proven and regulatory acceptable materials. A GDD of the present disclosure can provide for: improvements in surgical implantation technique; good post-operative outcomes; patient comfort; and/or a device service-life beyond five (5) years of surgical implantation, five (5) years typically being the service-life of presently available GDDs after surgical implantation.

A first aspect of the present disclosure provides a plate for an implantable ocular device, wherein the plate can comprise: a flexible material; and a tube retaining structure integrally formed with the plate; wherein the tube retaining structure is configured to secure a tube to the plate when the tube is moved. In some embodiments, the implantable ocular device can comprise an ocular drainage device. In some embodiments, the implantable ocular device can comprise a glaucoma drainage device.

In some embodiments, the tube retaining structure can comprise a low profile ridge. In some embodiments, the tube retaining structure can comprise a tube receiving channel having a horseshoe shape.

In some embodiments, the plate can further comprise at least one plate channel. In some embodiments, the at least one plate channel can be undercut into the plate. In some embodiments, the at least one plate channel can comprise a diameter that corresponds with an outer diameter of the tube.

In some embodiments, the plate can further comprise a reservoir. In some embodiments, the reservoir can be recessed.

In some embodiments, the plate can further comprise a material comprising collagen covering at least a portion of a top surface of the plate and/or at least a portion of the reservoir. In some embodiments, the material comprising collagen can comprise a material comprising pericardium, pericardial tissue, a pericardial patch, donor sclera or a combination of one or more thereof.

In some embodiments, the plate can further comprise a viscoelastic substance covering at least a portion of a top surface of the plate and/or at least a portion of the reservoir. In some embodiments, the viscoelastic material can cover at least a portion of the material comprising collagen.

In some embodiments, the plate can comprise a width (left to right) of about 24 mm or less. In some embodiments, the plate can comprise a length (front to back) of about 16 mm or less. In some embodiments, the plate can comprise a surface area of between about 250 mm$^2$ and about 360 mm$^2$.

In some embodiments, the plate can further comprise a tube receiving hole, wherein the tube receiving hole can comprise a diameter that corresponds to the outer diameter of the tube.

A second aspect of the present disclosure provides a tube for an implantable ocular device, wherein the tube can comprise: a length having a proximal end and a distal end; and a biodegradable cuff.

A third aspect of the present disclosure provides a tube for an implantable ocular device, wherein the tube can comprise: a length having a proximal end and a distal end; and an outer diameter of 0.7 mm or less.

A fourth aspect of the present disclosure provides a tube for an implantable ocular device, wherein the tube can comprise: a length having a proximal end and a distal end; wherein the distal end is bevelled.

A fifth aspect of the present disclosure provides a tube for an implantable ocular device, wherein the tube can comprise: a length having a proximal end and a distal end; and one or more micro-holes.

In some embodiments, the tube described above can comprise a drainage tube. In some embodiments, the implantable ocular device can comprise an ocular drainage device. In some embodiments, the implantable ocular device can comprise a glaucoma drainage device.

In some embodiments, the tube described above can comprise a length of between about 10 mm to about 20 mm. In some embodiments, the tube can comprise an inner diameter of about 0.3 mm or less. In some embodiments, the tube can comprise an inner diameter of about 0.1 mm to about 0.3 mm. In some embodiments, the tube can comprise an inner diameter of about 0.1 mm or less.

In some embodiments, the one or more micro-holes can comprise an inner diameter that is equal to about the size of the inner diameter of the tube. In some embodiments, the tube can further comprise two or more micro-holes, wherein the two or more micro-holes are positioned along the same axis along the length of the tube. In some embodiments, the tube can further comprise two or more micro-holes, wherein the two or more micro-holes are staggered along the length of the tube.

In some embodiments, the proximal end of the tube can be removably attached to a plate of the implantable ocular device, and wherein the distal end is configured for insertion into an eye. In some embodiments, the bevelled distal end of the tube can be bevelled at about 30°.

In some embodiments, the biodegradable cuff can comprise a material comprising PLGA (poly(lactic-co-glycolic) acid), PDLGA (poly(DL-lactide-co-glycolide)), a biodegradable polymer, a biocompatible polymer or a combination of one or more thereof.

In some embodiments, the biodegradable cuff can comprise a length that conforms to the curvature of an eye. In some embodiments, the biodegradable cuff can comprise a length of about 2 mm or less. In some embodiments, the biodegradable cuff can comprise a diameter that causes an inner diameter of the tube to be narrowed, wherein the narrowed inner diameter of the tube allows a fluid flow rate of about 2 µL/min or less through the tube. In some embodiments, the biodegradable cuff can comprise a wall thickness of about 0.5 mm or less.

In some embodiments, the biodegradable cuff can begin to degrade mechanically, structurally, or compositionally between about 4 weeks after implantation and about 8 weeks after implantation but not earlier than 4 weeks after implantation and not later than 8 weeks after implantation.

In some embodiments, the biodegradable cuff can be positioned between about 6 mm to about 10 mm from the distal end of the tube.

A sixth aspect of the present disclosure provides an implantable ocular device that can comprise: the plate described above; and the tube described above. In some embodiments, the implantable ocular device can comprise an ocular drainage device. In some embodiments, the implantable ocular device can comprise a glaucoma drainage device.

A seventh aspect of the present disclosure provides a method of manufacturing the plate described above, wherein the method can comprise: providing a medical grade elastomer material; and moulding the medical grade elastomer material. In some embodiments, the method of manufacturing the plate can further comprise polishing the moulded medical grade elastomer material.

An eighth aspect of the present disclosure provides a method of manufacturing the tube described above, wherein the method can comprise: providing a medical grade elastomer material; and extruding the medical grade elastomer material to form the tube.

A ninth aspect of the present disclosure provides a method of manufacturing the implantable ocular device described above, wherein the method can comprise: providing the plate described above; and providing the tube described above.

In some embodiments, the method of manufacturing the implantable ocular device described above can further comprise threading the tube through a tube receiving hole. In some embodiments, the method of manufacturing the implantable ocular device described above can further comprise threading the tube through a tube receiving hole by hand.

In some embodiments, the method of manufacturing the implantable ocular device described above can further comprise over-moulding the plate onto the tube.

A tenth aspect of the present disclosure provides a method of implanting the implantable ocular device described above, wherein the method can comprise: forming in an eye a sub-Tenon's/subconjunctival pocket having a size corresponding to the size of the plate; placing the plate over the sclera of the eye in the subconjunctiva pocket and securing the plate with sutures; and inserting the distal end of the tube into the anterior chamber of the eye; and customizing the length of the tube via cutting the proximal end of the tube.

An eleventh aspect of the present disclosure provides a method of controlling intra-ocular pressure, wherein the method can comprise: providing the implantable ocular device described above; and implanting the implantable ocular device described above into an eye using the method of implanting the implantable ocular device described above.

A twelfth aspect of the present disclosure provides a method of preventing complications associated with presently available glaucoma drainage devices, wherein the method can comprise: providing the implantable ocular device described above; and implanting the implantable ocular device described above into an eye using the method of implanting the implantable ocular device described above.

A thirteenth aspect of the present disclosure provides a stability system for an implantable ocular device, wherein the stability system can comprise: a plate; a material comprising collagen covering at least a portion of a top surface of the plate; and/or a viscoelastic substance covering at least a portion of a top surface of the plate. In some embodiments, the plate can comprise a reservoir.

BRIEF DESCRIPTION OF DRAWINGS

Embodiments of the present disclosure are described herein with reference to the drawings in which:

FIG. 2A-FIG. 2C illustrate different views of a plate in accordance with an embodiment of the present disclosure, wherein the plate comprises a tube retaining structure that includes a ridge. FIG. 2D-FIG. 2E illustrate a plate in accordance with an embodiment of the present disclosure, wherein the plate comprises a tube retaining structure that includes a horseshoe structure. FIG. 2F illustrates a plate in accordance with an embodiment of the present disclosure, wherein the plate includes more than one plate channel.

FIG. 3B illustrates a cross-section view of a tube retaining structure of a plate in accordance with an embodiment of the present disclosure, wherein the tube retaining structure comprises a ridge.

FIG. 7A shows the IOP trend of all patient/subject eyes of an experimental group (the group treated with the modified presently available glaucoma drainage device implant) and all patient/subject eyes of a control group (the group treated with the unmodified presently available glaucoma drainage device implant) before and after surgery with 6 months of follow up. FIG. 7B shows the number of anti-glaucoma medications required by the experimental group treated with the Tutopatch and Healaflow and the number of anti-glaucoma medications required by the control group without the Tutopatch and Healaflow before and after surgery with 6 months of follow up.

FIGS. 8B and 8D respectively show a first and a second set of simulated eye pressure versus flow trends, indicating a relationship between pressure and fluid flow through the modified Baerveldt device. FIGS. 8E and 8G respectively show a first set and a second set of simulated eye pressure drop trends versus time, using a glaucoma drainage device (GDD) 2 in accordance with the present disclosure; and FIGS. 8F and 8H respectively show a first and a second set of simulated eye pressure versus flow trends, indicating a relationship between pressure and fluid flow through such a glaucoma drainage device (GDD) 2 in accordance with the present disclosure changes with pressure.

FIG. 9A shows three sets of simulated eye pressure versus flow trends using the modified Baerveldt device. FIG. 9B shows the average of the three sets of simulated eye pressure versus flow trends of FIG. 9A. FIG. 9C shows two sets of simulated eye pressure versus flow trends, using a glaucoma drainage device (GDD) 2 in accordance with the present disclosure; and FIG. 9D shows the average of the two sets of simulated eye pressure versus flow trends of FIG. 9C.

DETAILED DESCRIPTION

Figure 1A:
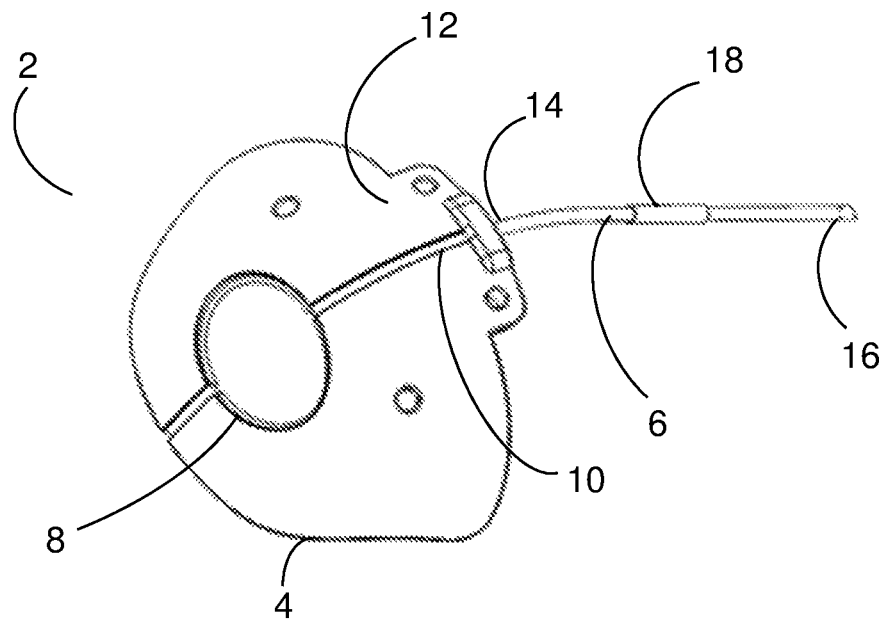
FIG. 1A-FIG. 1B illustrate different views of a glaucoma drainage device (GDD) in accordance with an embodiment of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented herein. Unless specified otherwise, the terms "comprising" and "comprise" as used herein, and grammatical variants thereof, are intended to represent "open" or "inclusive" language such that they include recited elements but also permit inclusion of additional, un-recited elements. As used herein, the term "about" in the context of concentrations of components, conditions, measurement or calculated values, etc., means+/−10% of the stated value, for instance, +/−5% of the stated value, or +/−4% of the stated value, or +/−3% of the stated value, or +/−2% of the stated value, or +/−1% of the stated value, or +/−0.5% of the stated value, or +/−0% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Glaucoma Drainage Device

Embodiments in accordance with the present disclosure are directed to glaucoma drainage devices that are structured in a manner that (a) greatly facilitates ease of implantation, and manipulation during an implantation procedure; (b) greatly facilitates maintenance of post-operative anterior chamber stability; (c) nearly or essentially eliminates post-operative complications such as hypotony; and (d) reduces or minimizes complications typically associated with implantation in shallow anterior chamber situations, and hence is suitable for use in such situations.

Figure 1B:
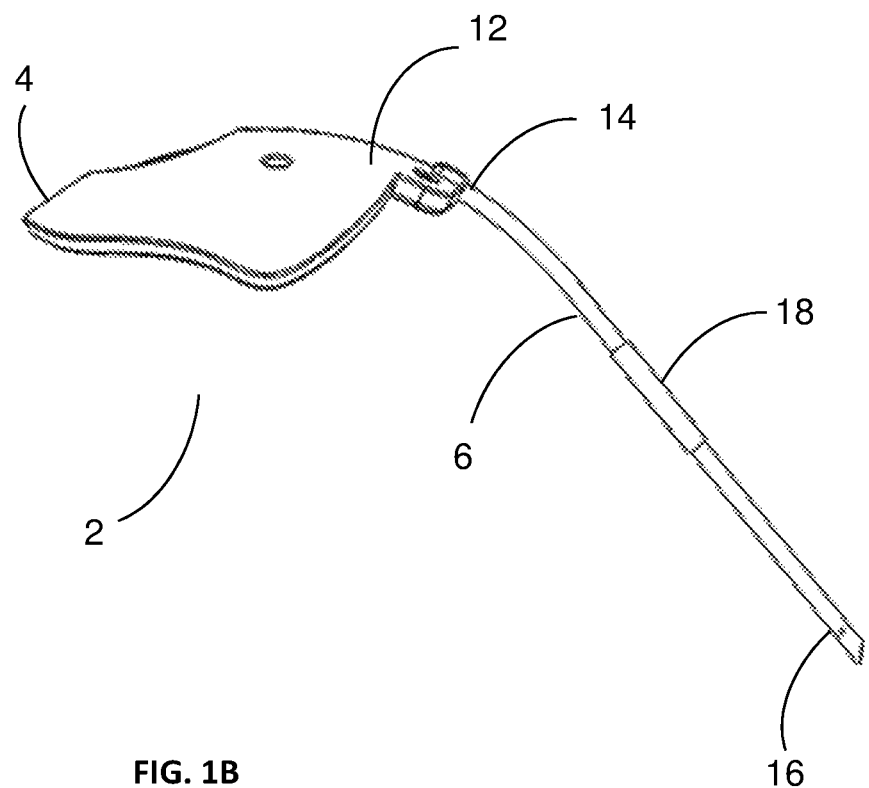

FIG. 1A-FIG. 1B illustrate different views of a glaucoma drainage device (GDD) 2 in accordance with an embodiment of the present disclosure. The GDD 2 can comprise a plate 4 and a tube 6 (e.g., a plate 4 configured to carry an elongate tube 6 along portions of the tube's length). The tube 6 can comprise a drainage tube 6. The tube 6 can comprise an anterior chamber tube 6. In some embodiments, the tube 6 can be adjustable and/or modifiable.

In some embodiments, the plate 4 can comprise a reservoir 8. The reservoir 8 on and/or in the plate 4 can act as a collection point for aqueous humor during implantation of the GDD 2, which can result in improved bleb formation. In some embodiments, the reservoir 8 can hold a material comprising collagen over and/or around portions of the plate 4. In some embodiments, the material comprising collagen can further comprise elastin. In some embodiments, the material comprising collagen can comprise pericardium, pericardial tissue and/or donor sclera. In some embodiments, the material comprising collagen can be flexible. In some embodiments, the material comprising collagen can be freeze-dried. In some embodiments, the material comprising collagen can comprise a patch.

In some embodiments, the reservoir 8 can hold a viscoelastic substance over and/or around the plate 4. In some embodiments, the viscoelastic substance can comprise sodium hyaluronate and/or a cross-linked hyaluronic acid. In some embodiments, the viscoelastic substance can comprise an inert viscoelastic substance.

In some embodiments, the reservoir 8 can hold the material comprising collagen over and/or around the plate 4 and/or can hold the viscoelastic substance over and/or around the plate 4.

In some embodiments, the plate 4 excludes or does not comprise a reservoir. In some embodiments, where the plate 4 does not comprise a reservoir, the material comprising collagen and/or the viscoelastic substance can be applied over and/or around portions of the plate 4.

In some embodiments, the plate 4 can comprise a plate channel 10 or plate channels 10 on and/or in the plate 4. The tube 6 can be inserted into the plate channel 10. The plate channel 10 can allow for the tube 6 to be cut to the desired length and fitted into the plate channel 10. The plate channel 10 can be used to secure the tube 6 on and/or in the plate 4 during implantation and post-implantation. In some embodiments, the plate channel 10 can be undercut into the upper surface 12 of the plate 4 such that the plate channel 10 comprises a length wherein a concave shape extends along the length of the plate channel 10. The concave shape extending along the length of the plate channel 10 can hold and/or secure the tube 6 in the plate channel 10.

The plate 4 can allow for improved implantation, improved anchoring, and/or improved fluid dissipation into the sub-conjunctival space. In some embodiments, the plate 4 can be made of a flexible material (e.g., silicone). In some embodiments, the plate 4 can have a low profile. The low profile of the plate 4 can allow the plate 4 to occupy less orbital volume such that there can be ease of insertion of the plate 4 and/or ease of conjunctiva closure during implantation. The low profile of the plate 4 can also result in improved bleb formation. The low profile of the plate 4 can result in less extrusion through the conjunctiva and/or less stretching of the conjunctiva, which subsequently can result in improved bleb formation. In the long-term, a good bleb can allow for better eyeball mobility and fluid flow control in a patient.

In some embodiments, the plate 4 can be treated (e.g., by way of surface polishing) to give the plate 4 a smooth profile. The smooth profile can reduce fibrosis and/or scar tissue thereby resulting in improved bleb formation. In some embodiments, the plate 4 can be made of a flexible material (e.g., silicone), wherein the flexible material can have a modulus that is similar to that of the sclera. The plate 4 and/or the adjustable tube 6 can allow for easier implantation of the GDD 2 into a patient as well as reduce discomfort for the patient after implantation.

In some embodiments, the tube 6 can comprise a length having a proximal end 14 for insertion into the plate channel 10 and a distal end 16 for insertion into the eye. In some embodiments, the tube 6 can comprise or carry a cuff 18 situated and/or positioned along a section of the length of the tube 6, wherein the cuff 18 covers the outer surface circumference defined by the section of the tube 6. In some embodiments, the cuff 18 can comprise a biodegradable cuff 18 or biocompatible erodible cuff 18, wherein the cuff 18 can be situated and/or positioned along a section of the length of the tube 6, wherein the cuff 18 covers the outer surface circumference defined by the section of the tube 6.

The distal end 16 of the tube 6 can be inserted into the anterior chamber of a patient's eye. In some embodiments, the tube 6 can be adjustable and/or modifiable. In some embodiments, the design of the tube 6 allows the surgeon or clinician to customize the tube 6 to the required length for each patient while the proximal end 14 of the tube 6 remains connected/attached to the plate 4 and while the distal end 16 of the tube 6 remains in the anterior chamber of the patient's eye. Once the desired length is identified, the proximal end 14 of the tube 6 can be cut while the distal end 16 of the tube 6 remains in the anterior chamber of the patient's eye. In contrast, the current practice with presently available GDDs is to either cut a distal end of a tube to a desired length based on estimation or insert a distal end of a tube into the eye, identify a desired length, take the distal end of the tube out of the eye, cut the distal end of the tube, and then re-insert the cut distal end of the tube back into the eye.

In some embodiments, the distal end 16 of the tube 6 can be smooth such that the distal end 16 will have atraumatic edges thereby further reducing any potential injury to the patient during tube 6 insertion and retention in the eye. In some embodiments, the distal end 16 of the tube 6 does not comprise a cut edge that can injure the eye. In contrast, the current practice with presently available GDDs is to cut the tube at a distal end in order to achieve the desired length of the tube, wherein the cut distal end can have an edge or edges that can potentially injure the eye upon insertion and/or retention.

In some embodiments, the tube 6 can have a reduced profile (e.g., a reduced diameter and/or a small diameter) to prevent damage to the intra-ocular tissues.

In some embodiments, the proximal end 14 of the tube 6 is connected to the plate 4 while the distal end 16 of the tube 6 is placed or inserted in the anterior chamber (AC) of the eye. The plate 4 can be implanted under the conjunctiva. Once attached to the eye, excess fluid can be drained out from the AC via the tube 6 and dissipated through the plate 4 thereby reducing excess intra-ocular pressure (IOP).

In some embodiments, the cuff 18 can be situated and/or positioned along a section of the length of the tube 6. In some embodiments, the cuff 18 situated and/or positioned along a section of the length of the tube 6 can reduce the original diameter of the section of the tube 6 that the cuff 18 covers from the outer lumen to restrict and/or control fluid flow during the first four (4) to eight (8) weeks after implantation of the GDD 2. As the cuff 18 degrades, the cuff 18 slowly reduces constriction on the section of the tube 6 that the cuff 18 covers thereby gradually releasing and/or gradually allowing the section of the tube 6 that the cuff 18 covers to revert back to the original diameter of the section of the tube 6.

In some embodiments, the cuff 18 situated and/or positioned on a section of the length of the tube 6 can create resistance to rapid fluid flow for up to a minimum of about four (4) weeks after implantation thereby preventing excessive fluid drainage that can lead to hypotony in the early phase (e.g., before fibrous tissue formation over the plate 4 of the GDD 2) and up to a maximum of about eight (8) weeks after implantation thereby allowing additional outflow to minimize excess fluid retention that can cause post-operative raised IOP.

In some embodiments, the cuff 18 can begin to degrade and/or dissipate (and thereby begin to lose its mechanical strength and/or mechanical properties) between about four (4) weeks after implantation to about eight (8) weeks after implantation but not earlier than 4 weeks after implantation and not later than 8 weeks after implantation.

In some embodiments, the cuff 18 can begin to degrade (and thereby begin to lose its mechanical strength and/or mechanical properties) not earlier than four (4) weeks after implantation thereby preventing excessive fluid drainage that can lead to hypotony in the early phase (e.g., before fibrous tissue formation over the plate 4 of the GDD 2) and not later than eight (8) weeks after implantation thereby allowing additional outflow to minimize excess fluid retention that can cause post-operative raised IOP.

Thus, the cuff 18 can restrict and/or control the initial fluid flow out of the eye to prevent hypotony prior to the formation of a fibrous tissue over the plate 4. Additionally, the gradual degradation of the mechanical strength and/or mechanical properties of the cuff 18 can prevent post-operative raised IOP at a later phase (e.g., post formation of a fibrous tissue over the plate).

In some embodiments, the diameter of the section of the tube 6 that the cuff 18 covers can increase in size to its original diameter and/or final diameter at about eight (8) weeks after implantation thereby influencing the rate of fluid exiting the eye by allowing for an increase in fluid flow. In some embodiments, the diameter of the section of the tube 6 that the cuff 18 covers can increase in size to its original diameter and/or final diameter after about eight (8) weeks after implantation thereby influencing the rate of fluid exiting the eye by allowing for an increase in fluid flow.

In some embodiments, the cuff 18 can still have a physical presence after losing its mechanical strength and/or mechanical properties. In some embodiment, the cuff 18 can still have a physical presence after degrading to lose its mechanical strength and/or mechanical properties and/or after dissipating to lose its mechanical strength and/or mechanical properties.

In some embodiments, the cuff 18 can fully degrade and fully lose its mechanical strength and/or mechanical properties at about eight (8) weeks after implantation or after about eight (8) weeks after implantation.

In some embodiments, the cuff 18 can fully degrade and fully lose its mechanical strength and/or mechanical properties at about eight (8) weeks after implantation or after about eight (8) weeks after implantation such that the diameter of the section of the tube 6 that the cuff 18 covers can increase to the original diameter of the tube 6 prior to situating and/or positioning the cuff 18 on the tube 6.

At about four (4) weeks after implantation some degree of fibrous encapsulation will have developed around the plate 4 portion of the GDD 2 creating some resistance to fluid flow and preventing hypotony.

FIG. 2A-FIG. 2F illustrate a plate 4 in accordance with embodiments of the present disclosure.

Figure 2A:
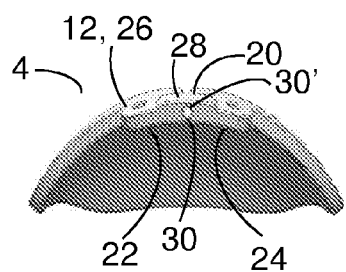
FIG. 2A-FIG. 2F illustrate a plate in accordance with embodiments of the present disclosure. In particular.
Figure 2B:
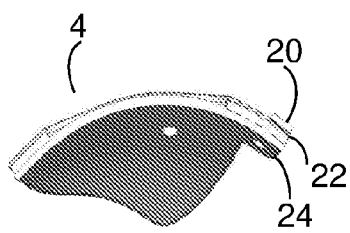
Figure 2C:
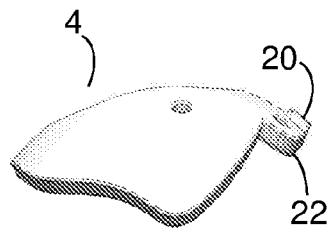

FIG. 2A-FIG. 2C illustrate different views of a plate 4 in accordance with an embodiment of the present disclosure, wherein the plate 4 comprises a tube retaining structure 20. In some embodiments, the tube retaining structure 20 can comprise a ridge 20. In some embodiments, the plate 4 can be integrally formed with the tube retaining structure 20. In some embodiments, the plate 4 can be integrally formed with the ridge 20.

In some embodiments, the ridge 20 can comprise a low profile. In some embodiments, the ridge 20 can comprise a height of about 0.3 mm or less, wherein the total height of the plate 4 (including the both the plate height and ridge height) is about 1.3 mm or less. In some embodiments, the ridge 20 can comprise a height of about 0.3 mm or less, wherein the total height of the plate 4 is about 1.25 mm or less. In some embodiments, the ridge 20 can comprise a length of between at least 2 mm to about 4 mm. In some embodiments, the ridge 20 can comprise a length of about 4 mm. In some embodiments, the ridge 20 can comprise a width of at least about 1 mm. In some embodiments, the ridge 20 can comprise a width of about 1 mm.

The low profile ridge 20 can allow the plate 4 to have a reduced profile for improved bleb formation. In other words, the plate 4 comprising the ridge 20 can have an overall reduced thickness and/or an overall reduced height thereby resulting in improved bleb formation.

In some embodiments, the low profile ridge 20 of the plate 4 can contribute to improved bleb formation post implantation. In some embodiments, the reservoir 8 on the plate 4 can contribute to improved bleb formation post implantation. In some embodiments, both the low profile ridge 20 of the plate 4 and the reservoir 8 on the plate 4 can contribute to improved bleb formation post implantation.

In some embodiments, the reservoir 8 can hold a material comprising collagen (e.g., pericardium, pericardial tissue and/or donor sclera) in place over and/or around the plate 4. In some embodiments, the material comprising collagen can be flexible. In some embodiments, the material comprising collagen can be freeze dried. In some embodiments, the material comprising collagen can comprise a patch.

In some embodiments, the reservoir 8 can hold a viscoelastic substance (e.g., sodium hyaluronate and/or cross-linked hyaluronic acid) in place over and/or around the plate 4. In some embodiments, the viscoelastic substance can comprise an inert viscoelastic substance.

In some embodiments, the reservoir 8 can hold a material comprising collagen (e.g., pericardium, pericardial tissue and/or donor sclera), a viscoelastic substance (e.g., sodium hyaluronate and/or cross-linked hyaluronic acid) or a combination thereof in place over and/or around the plate 4.

Referring to FIG. 2A-FIG. 2C, in accordance with an embodiment of the present disclosure, the plate 4 can comprise a tube receiving end 22, wherein the tube receiving end 22 comprises a bottom surface 24 and a top surface 12, 26, wherein the tube receiving end 22 is integrally formed with a tube retaining structure 20, wherein the tube retaining structure 20 comprises a ridge 20, wherein the ridge 20 is formed proximate to and/or on the top surface 12, 26 of the tube receiving end 22, wherein the ridge 20 comprises a top exposed surface 28 and a width, wherein a tube receiving hole 30, aperture 30 or opening 30 is disposed and/or formed at a section between the bottom surface 24 of the tube receiving end 22 and the top exposed surface 28 of the ridge 20, wherein the tube receiving hole 30 is integrally formed with and/or integrally connected to a tube receiving channel 30', wherein the tube receiving channel 30' comprises a length, wherein the length of the tube receiving channel 30' extends along the entire width of the ridge 20, wherein the plate 4 further comprises a plate channel 10, wherein the tube receiving channel 30' is connected to the plate channel 10.

In some embodiments, the tube receiving channel 30' can be integrally formed with and/or integrally connected to the plate channel 10.

In some embodiments, the tube receiving channel 30' can comprise a cylindrical shape, wherein the tube receiving channel 30' can cover the entire circumference of the tube 6.

In some embodiments, the outer diameter of the tube 6, the diameter of the concave shape extending along of the entire length of the plate channel 10, the diameter of the tube receiving hole 30, and the diameter of the tube receiving channel 30' can be about the same size or equivalent in size.

In accordance with an embodiment of the present disclosure, the plate 4, tube receiving end 22, tube retaining structure 20, ridge 20, tube receiving hole 30, and tube receiving channel 30' can be integrally formed as one structure. In some embodiments, the plate 4, tube retaining structure 20, ridge 20, tube receiving hole 30, and tube receiving channel 30' can be integrally formed as one structure via a moulding process.

In some embodiments, the proximal end 14 of the tube 6 can be inserted into the tube receiving hole 30 and subsequently inserted into the tube receiving channel 30'. The tube receiving channel 30' can extend along the entire width of the ridge 20 and be connected to the plate channel 10. The ridge 20 can be used to secure and/or hold the tube 6 in the tube receiving hole 30 and tube receiving channel 30' during: movement and/or displacement of the tube 6; movement and/or displacement of the tube 6 during implantation; the implantation procedure; and/or post-implantation.

For example, once the tube 6 is inserted into the tube receiving hole 30 and subsequently into the tube receiving channel 30', and secured and/or held in the tube receiving hole 30 and/or tube receiving channel 30' by the ridge 20, the length of the tube 6 can be adjusted or modified by pulling, pushing, displacing, sliding and/or moving the tube 6 distally (i.e., away from the plate 4) to increase the length of the tube 6 (beyond the receiving hole 30 and/or by pulling, pushing, displacing, sliding and/or moving the tube 6 proximally (i.e., toward the plate 4) to shorten the length of the tube 6 (beyond the receiving hole 30). After the tube 6 is inserted into the tube receiving hole 30 and subsequently into the tube receiving channel 30', and secured and/or held in the tube receiving hole 30 and/or tube receiving channel 30' by the ridge 20, the tube 6 can be pulled, pushed, displaced and/or moved without being removed from the plate 4 because the ridge 20 holds the tube 6 firmly or securely in place in the tube receiving channel 30'. The tube 6 can be pulled, pushed and/or moved from the tube receiving end 22 of the plate 4 to the reservoir 8 and/or the opposite end of the plate 4.

As such, any excess tube 6 length can be cut from the 14 proximal end of the tube 6 extending proximally away from the ridge 20 while the tube 6 remains secured in the tube receiving channel 30' covered by the ridge 20 and extending along the width of the ridge 20. Thus, the tube 6 does not need to be removed from the plate 4 in order to modify or adjust the length of the tube 6 at the proximal end 14 of the tube 6. In addition, the distal end 16 of the tube 6 does not need to be removed from the anterior chamber (AC) of the eye at any time during the modification or adjustment of the length of the tube 6.

If required, the tube 6 can be removed from the tube receiving channel 30' and plate 4 by pulling and/or pushing the tube 6 distally away from the plate 4.

Figure 2D:
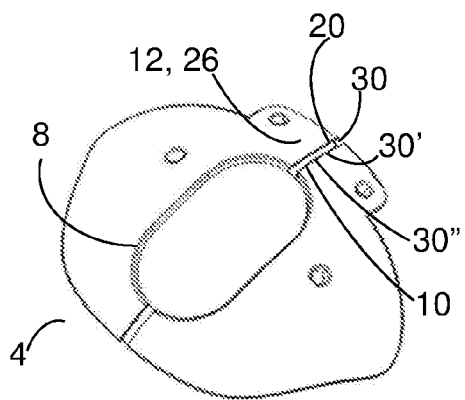
Figure 2E:
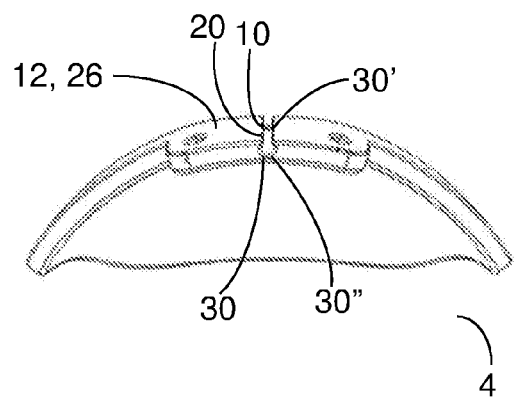

Referring to FIG. 2D-FIG. 2E, in some embodiments, a tube receiving hole 30 and tube receiving channel 30' can be formed in the plate 4 such that the tube receiving channel 30' secures and/or holds the tube 6 in the tube receiving channel 30'. In such embodiments, the tube receiving channel 30' can act as a tube retaining structure 20. For example, a tube receiving channel 30' can be undercut into the 12 top surface of the plate 4, wherein the tube receiving channel 30' comprises a length, wherein a horseshoe shape 30" extends along the entire length of the tube receiving channel 30', wherein the horseshoe shape 30" of the tube receiving channel 30' allows the tube receiving channel 30' to act as a tube retaining structure 20 such that the tube 6 can be pulled proximally and distally through the tube receiving channel 30' without being removed from the tube receiving channel 30'.

In some embodiments, the tube receiving channel 30' can cover the entire circumference of the tube 6, wherein no part of the circumference of the tube 6 section sitting in the tube receiving channel 30' is exposed. In some embodiments, the tube receiving channel 30' can cover a substantial part of the circumference of the tube 6, wherein a portion of the circumference of the tube 6 section sitting in the tube receiving channel 30' can be exposed. In some embodiments, the tube receiving channel 30' can cover a first portion of the circumference of the tube 6, wherein a second portion of the circumference of the tube 6 section sitting in the tube receiving channel 30' can be exposed.

In some embodiments, the entire circumference of the tube 6 can sit in the plate channel 10, wherein a portion of the circumference of the tube 6 can be exposed. In some embodiments, a substantial part of the circumference of the tube 6 can sit in the plate channel 10, wherein a portion of the circumference of the tube 6 can be exposed. In some embodiments, a first portion of the circumference of the tube 6 can sit in the plate channel 10, wherein a second portion of the circumference of the tube 6 can be exposed.

Figure 2F:
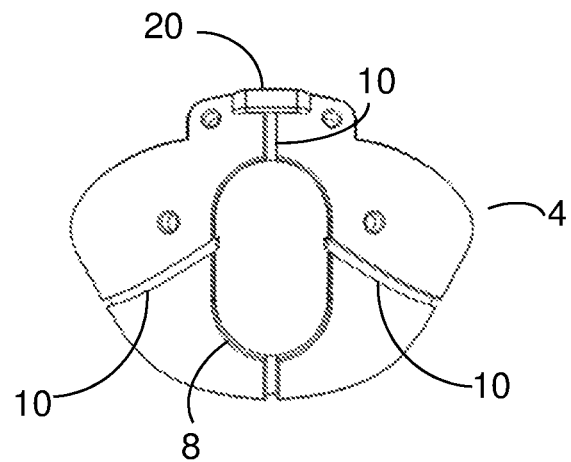

As illustrated in FIG. 2F, in some embodiments, a plate 4 can comprise one or more plate channels 10. In some embodiments, a plate 4 can have one or more undercut plate channels 10. In some embodiments, the one or more plate channels 10 can run from the tube retaining structure 20 (e.g., the ridge 20 or the tube receiving channel 30' comprising a horseshoe shape 30" that acts as a tube retaining structure 20) to the reservoir 8 and/or from the reservoir 8 to one or more ends of the plate 4.

In some embodiments, the one or more undercut plate channels 10 can be formed by removing material from the plate 4 to form the one or more plate channels 10. The one or more undercut plate channels 10 can allow the GDD 2 to have an overall lower profile (e.g., a reduced thickness and/or a reduced height). For example, in accordance with some embodiments of the present disclosure, the one or more undercut plate channels 10 can allow the tube 6 to recess into the plate 4 so that the overall profile of the GDD 2 is only as high as the height of the tube retaining structure 20 (e.g., the ridge 20 or the tube receiving channel 30' comprising a horseshoe shape 30" that acts as a tube retaining structure 20).

In some embodiments, as illustrated in FIG. 2A-FIG. 2C, the tube retaining structure 20 can comprise a ridge 20. In some embodiments, the ridge 20 can comprise a low profile ridge 20. In some embodiments, the one or more undercut plate channels 10 can allow the tube 6 to recess into the plate 4 so that the overall profile of the GDD 2 is only as high as the height of the ridge 20. In some embodiments, the one or more undercut plate channels 10 can allow the tube 6 to recess into the plate 4 so that the overall profile of the GDD 2 is only as high as the height of the low profile ridge 20.

In some embodiments, as illustrated in FIG. 2D-FIG. 2E, the tube retaining structure 20 can comprise a tube receiving channel 30', wherein the tube receiving channel 30' comprises a length, wherein a horseshoe shape 30" extends along the entire length of the tube receiving channel 30', wherein the horseshoe shape 30" of the tube receiving channel 30' allows the tube receiving channel 30' to function and/or act as the tube retaining structure 20. In some embodiments, the one or more undercut plate channels 10 can allow the tube 6 to recess into the plate 4 so that the overall profile of the GDD 2 is only as high as the height of the tube retaining structure 20 comprising a tube receiving channel 30' comprising a horseshoe shape 30".

Figure 3A:
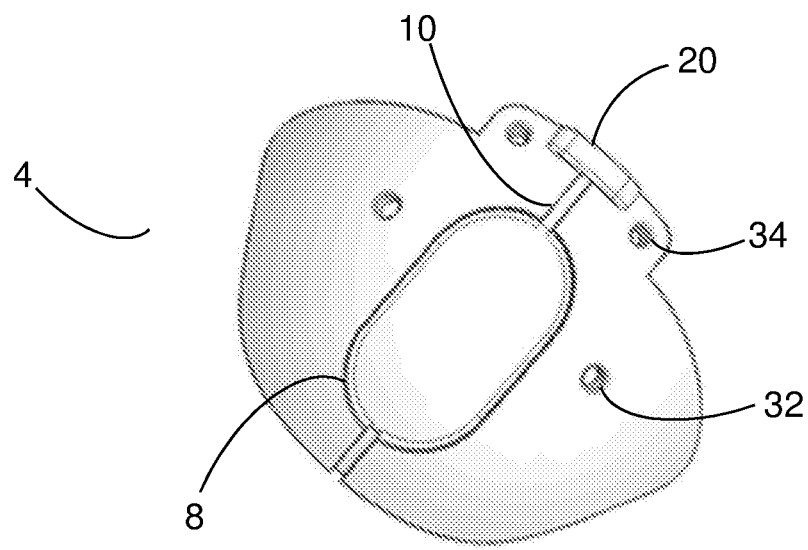
FIG. 3A-3B illustrate views of a plate in accordance with an embodiment of the present disclosure.
Figure 3B:
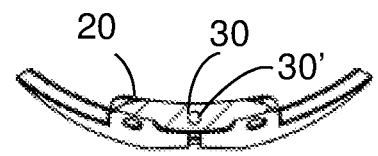
Figure 3B:
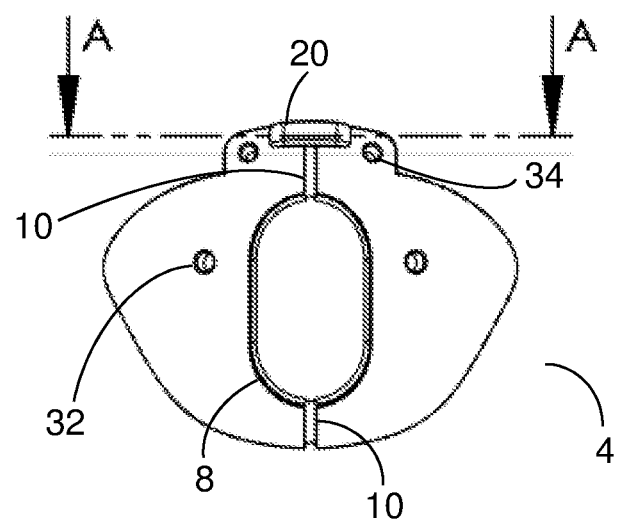

FIG. 3A-3B illustrate a plate 4 in accordance with an embodiment of the present disclosure. FIG. 3B illustrates a cross-section of a tube retaining structure 20 in accordance with an embodiment of the present disclosure, wherein the tube retaining structure 20 comprises a ridge 20, wherein the ridge 20 comprises a tube receiving hole 30 and a tube receiving channel 30', wherein a tube 6 can be inserted into the tube receiving hole 30 and subsequently into the tube receiving channel 30'.

In accordance with an embodiment of the present disclosure, a plate 4 of a GDD 2 can have a size and/or shape that allows for ease of implantation and/or good efficacy. In some embodiments, the plate 4 of the GDD 2 can have a recessed reservoir 8. In some embodiments, the plate 4 of the GDD 2 can have one or more undercut plate channels 10. In some embodiments, the plate 4 of the GDD 2 can comprise a tube retaining structure 20, wherein the tube retaining structure 20 comprises a low profile ridge 20. In some embodiments, the plate 4 of the GDD 2 can comprise a tube retaining structure 20, wherein the tube retaining structure 20 comprises a tube receiving channel 30' comprising a horseshoe shape 30", wherein the tube receiving channel 30' acts and/or functions as a tube retaining structure 20.

In some embodiments, the length (front to back) of the plate 4 can be about 16 mm or less. In some embodiments, the length (front to back) of the plate 4 can be about 16 mm. In some embodiments, the width (left to right) of the plate 4 can be about 24 mm or less. In some embodiments, the width (left to right) of the plate 4 can be about 24 mm. In some embodiments, the thickness of the plate 4 can be about 1 mm or less. In some embodiments, the thickness of the plate 4 can be about 1 mm.

In some embodiments, the surface area of the plate 4 can be between about 250 $mm^2$ and about 350 $mm^2$. In some embodiments, the surface area of the plate 4 can be between about 250 $mm^2$ and about 360 $mm^2$. In some embodiments, the surface area of the plate 4 can be about 267 $mm^2$, 302 $mm^2$, 313 $mm^2$ or 315 $mm^2$.

In some embodiments, the plate 4 can be flexible to allow the plate 4 to conform to the eye of the patient or subject. In some embodiments, the plate 4 can have a shore hardness of between about A60 and A80. In some embodiments, the plate 4 can have a shore hardness of about A80.

In some embodiments, the plate 4 can comprise at least one fenestration 32. In some embodiments, the plate 4 can comprise two fenestrations 32. In some embodiments, the plate 4 can comprise up to four (4) fenestrations 32. In some embodiments, each of the fenestrations 32 can have a diameter of about 0.95 mm.

In some embodiments, the plate 4 can comprise at least one suture hole 34. In some embodiments, the plate 4 can comprise two suture holes 34. In some embodiments, each of the suture holes 34 can have a diameter of about 0.8 mm.

In some embodiments, the surface of the plate 4 can be smooth and have a low profile. In some embodiments, the surface of the plate 4 can comprise a medical grade elastomer. In some embodiments, the surface of the plate 4 can comprise a medical grade silicone. In some embodiments, the surface of the plate 4 can be polished. In some embodiments, the surface of the plate 4 can comprise a polished medical grade silicone.

In some embodiments, the plate 4 can comprise a recessed area that forms a reservoir 8 for fluid accumulation. The reservoir 8 can have any shape. In some embodiments, the reservoir 8 can comprise an oval shape.

The plate 4 can comprise one or more plate channels 10 that can run from the tube retaining structure 20 (e.g., the ridge 20 or the tube receiving channel 30' comprising the horseshoe shape 30" that acts as a tube retaining structure 20) to the reservoir 8 and/or from the reservoir 8 to one or more ends of the plate 4.

The plate channel 10 can hold the tube 6 in place. In some embodiments, the plate 4 can comprise an undercutting of the plate channel 10 into the plate 4 in order that the tube 6 is flush with the plate 4 and the plate 4 is flush with the tube 6. In other words, the plate channel 10 can be undercut into the plate 4.

In some embodiments, the plate channel 10 can comprise a concave shape or arc extending along the entire length of the plate channel 10 that can secure the tube 6 in the plate channel 10. In some embodiments, the diameter of the plate channel 10 can be about the same size as the outer diameter of the tube 6 used. In some embodiments, the diameter of the plate channel 10 can correspond with the outer diameter of the tube 6, the diameter of the tube receiving hole 30, and/or the diameter of the tube receiving channel 30'. In some embodiments, the concave shape or arc extending along the entire length of the plate channel 10 can comprise a diameter of about 0.7 mm or less, about 0.63 or less, about 0.6 mm or less, about 0.45 mm or less, about 0.43 mm or less, or about 0.35 mm.

In some embodiments, the plate 4 can comprise a low profile ridge 20. The ridge 20 can aid in the control of bleb formation. The ridge 20 can hold the tube 6 to the plate 4 and can prevent the tube 6 from falling out while the tube 6 length is being adjusted. The ridge 20 can allow the tube 6 to move freely along the width of ridge 20 thereby allowing the tube length 6 to be altered or adjusted by altering or adjusting the proximal end 14 of the tube 6 length anterior to the ridge 18.

The diameter of the tube receiving hole 30 can correspond with the outer diameter of the tube 6, the diameter of the plate channel 10, and/or the diameter of the tube receiving channel. For example, in some embodiments, the tube receiving hole 30 can have a diameter of 0.7 mm or less, 0.63 mm or less, 0.6 mm or less, 0.45 mm or less, 0.43 mm or less, or 0.35 mm and the tube 6 can have an outer diameter of 0.7 mm or less, 0.63 mm or less, 0.6 mm or less, 0.45 mm or less, 0.43 mm or less, or 0.35 mm.

Figure 4A:
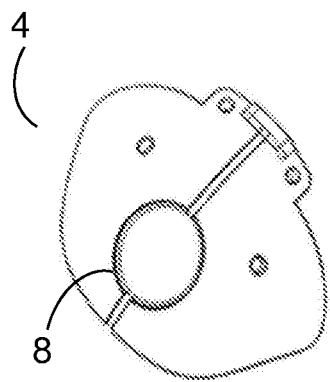
FIG. 4A-FIG. 4C illustrate plates in accordance with different embodiments of the present disclosure.
Figure 4B:
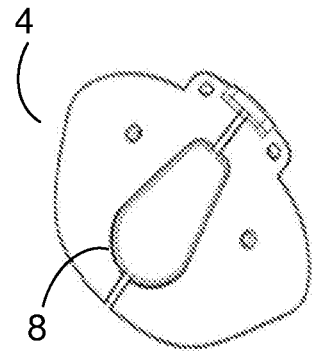
Figure 4C:
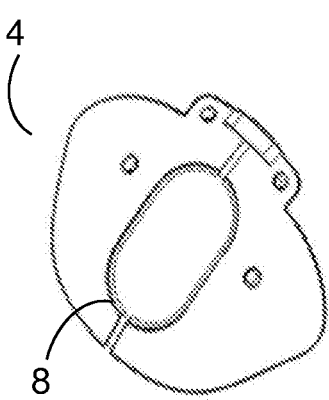

FIG. 4A illustrates a plate 4 of a GDD 2 in accordance with an embodiment of the present disclosure, wherein the reservoir 8 comprises a circular shape. FIG. 4B illustrates a plate 4 of a GDD 2 in accordance with an embodiment of the present disclosure, wherein the reservoir 8 comprises a bell shape or pear shape. FIG. 4C illustrates a plate 4 of a GDD 2 in accordance with an embodiment of the present disclosure, wherein the reservoir 8 comprises an oval shape. Other shapes for the reservoir 8 are also contemplated.

Figure 5A:
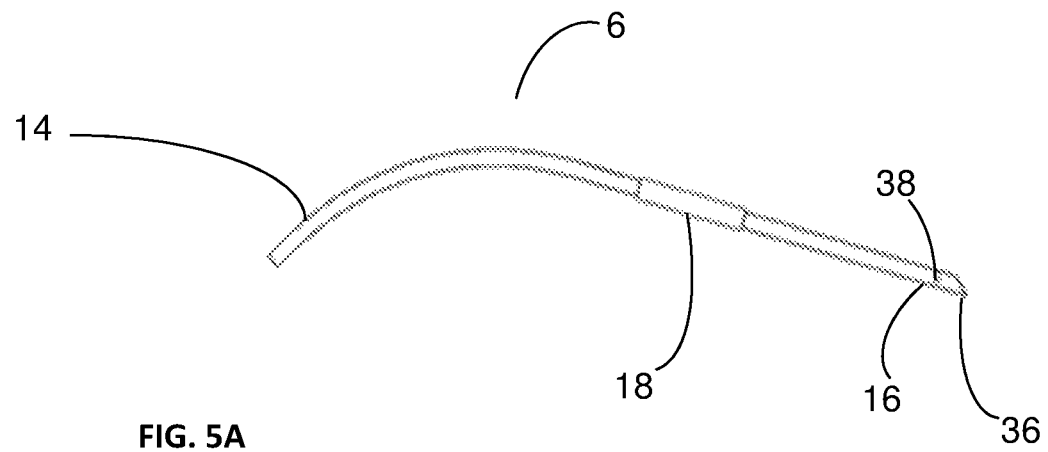
FIG. 5A-FIG. 5B illustrate different views of a tube in accordance with an embodiment of the present disclosure.
Figure 5B:
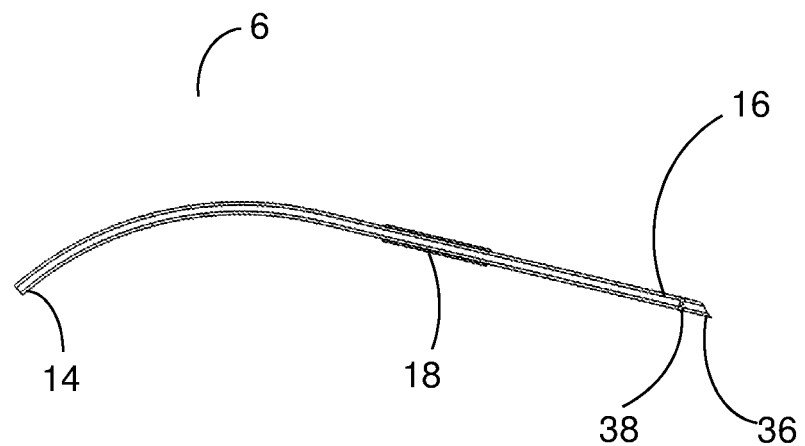

FIG. 5A-FIG. 5B illustrate different perspectives of a tube 6 in accordance with an embodiment of the present disclosure. The tube 6 can comprise a drainage tube 6. The tube 6 can comprise an anterior chamber tube 6. In some embodiments, the tube 6 can be adjustable and/or modifiable.

In some embodiments, the tube 6 can comprise a bevelled edge 36 at the distal end 16 of the tube 6. The bevelled edge 36 at the distal end 16 of the tube 6 can allow for easy insertion of the tube 6 into the eye. In some embodiments, the distal end 16 of the tube 6 can be bevelled at about 30°. In some embodiments, the bevelled edge 36 can be pre-cut. The pre-cut bevelled edge 36 can provide a tube 6 having an atraumatic profile that can prevent damage to the eye during insertion of the tube 6 and/or when the tube 6 is retained in the eye.

In some embodiments, the tube 6 can have a length of between about 10 mm and about 20 mm. In some embodiments, the tube 6 can have a length of about 17 mm. In some embodiments, the tube 6 can have a fixed length of about 17 mm.

In some embodiments, the tube 6 can have an outer diameter of about 0.7 mm or less. In some embodiments, the tube 6 can have an inner diameter of about 0.3 mm or less. In some embodiments, the tube 6 can have an outer diameter of about 0.45 mm or less. In some embodiments, the tube 6 can have an inner diameter of about 0.1 mm or less. In some embodiments, the tube 6 can have an outer diameter of about 0.43 mm or less. In some embodiments, the tube 6 can have an inner diameter of about 0.1 mm or less. In some embodiments, the tube 6 can have an outer diameter of about 0.35 mm. In some embodiments, the tube 6 can have an inner diameter of about 0.050 mm. In some embodiments, the tube 6 can have an outer diameter of about 0.63 mm. In some embodiments, the tube 6 can have an inner diameter of about 0.3 mm. In some embodiments, the tube 6 can have an outer diameter of about 0.6 mm. In some embodiments, the tube 6 can have an inner diameter of about 0.3 mm. In some embodiments, the tube 6 can have an inner diameter of about 0.1 mm to about 0.3 mm.

In some embodiments, the tube 6 can comprise a wall thickness of about 0.2 mm. In some embodiments, the tube 6 can comprise a wall thickness of about 0.165 mm. In some embodiments, the tube 6 can comprise a wall thickness of about 0.175 mm. In some embodiments, the tube 6 can comprise a wall thickness of about 0.15 mm.

In a number of embodiments, the tube's outer diameter, wall thickness, and inner diameter are selected such that the tube 6 exhibits both increased rigidity and a greater resistance to fluid flow compared to conventional commercially available tubes. Increased tube rigidity can aid or greatly aid insertion and manipulation of the tube 6 compared to conventional commercially available tubes, thereby making an overall implantation procedure simpler and less time consuming.

In some embodiments, the tube 6 can comprise a biodegradable cuff 18 or biocompatible erodible cuff 18 situated along a section of the length of the tube 6, wherein the cuff 18 covers the outer surface circumference defined by the section of the tube 6. The cuff 18 can function as a flow restrictor.

In some embodiments, the cuff 18 can comprise a biodegradable material comprising PLGA, PDLGA, a biodegradable polymer, a biocompatible polymer, or a combination of one or more thereof. In some embodiments, the cuff 18 can comprise PDLGA.

In some embodiments, the cuff 18 can comprise a length that conforms to the curvature of the eye. In some embodiments, the cuff 18 can comprise a length that conforms to the curvature of the eye of the patient or subject. In some embodiments, the cuff 18 can have a length of about 2 mm or less. In some embodiments, the cuff 18 can have a length of about 2 mm. In some embodiments, the cuff 18 can have a length of about 1 mm.

In some embodiments, the cuff 18 can comprise a diameter that causes the tube 6 to be narrowed to a diameter of about 10 microns. In some embodiments, the cuff 18 can comprise an outer diameter of about 1.0 mm. In some embodiments, the cuff 18 can comprise an inner diameter of about 0.5 mm. In some embodiments, the cuff 18 can comprise an outer diameter of about 0.9 mm. In some embodiments, the cuff 18 can comprise an inner diameter of about 0.35 mm. In some embodiments, the cuff 18 can comprise an outer diameter of about 0.85 mm. In some embodiments, the cuff 18 can comprise an inner diameter of about 0.35 mm. In some embodiments, the cuff 18 can comprise an outer diameter of about 0.86 mm. In some embodiments, the cuff 18 can comprise an inner diameter of about 0.36 mm.

In some embodiments, the cuff 18 can comprise a wall thickness of about 0.5 mm or less to provide a degradation rate that allows the cuff 18 to begin to degrade (and thereby begin to lose its mechanical strength and/or mechanical properties) between about four (4) weeks after implantation to about eight (8) weeks after implantation but not earlier than 4 weeks after implantation and not later than 8 weeks after implantation of the GDD 2.

In some embodiments, the cuff 18 can comprise a wall thickness of about 0.5 mm or less to provide a degradation rate that allows the cuff 18 to fully degrade (and thereby fully lose its mechanical strength and/or mechanical properties) at about eight (8) weeks after implantation or after about 8 weeks after implantation of the GDD 2.

The wall thickness of the cuff 18 and/or the material used to make the cuff 18 can determine the degradation rate of the cuff 18. In some embodiments, the cuff 18 can comprise a wall thickness of about 0.5 mm.

In some embodiments, the cuff 18 can comprise a biodegradable material that begins to degrade (and thereby begin to lose its mechanical strength and/or mechanical properties) between about four (4) weeks after implantation to about eight (8) weeks after implantation but not earlier than 4 weeks after implantation and not later than 8 weeks after implantation of the GDD 2. In some embodiments, the cuff 18 can comprise a biodegradable material that fully degrades (and thereby fully loses its mechanical strength and/or mechanical properties) at about eight (8) weeks after implantation or after about 8 weeks after implantation of the GDD 2 thereby allowing full fluid flow.

In some embodiments, the cuff 18 can be positioned over the tube 6 and between about 6 mm to about 10 mm from the distal end 16 of the tube 6. In some embodiments, the cuff 18 can be positioned over the tube 6 and about 8 mm from the distal end 16 of the tube 6. In some embodiments, the tube 6 can comprise a bevelled edge 36 or bevelled tip 36 at the distal end 16 of the tube 6.

In some embodiments, the tube 6 can comprise one or more micro-holes 38.

Figure 6A:
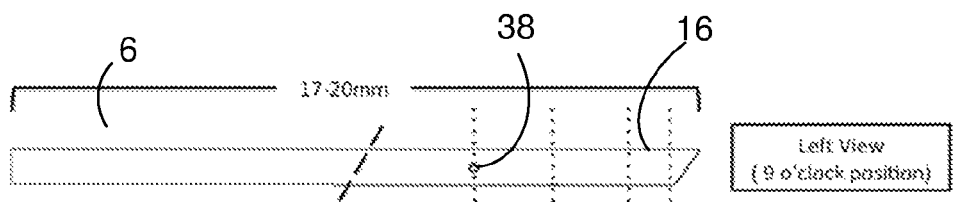
FIG. 6A-FIG. 6C illustrate different views of a tube in accordance with an embodiment of the present disclosure, wherein the tube comprises micro-holes.
Figure 6B:
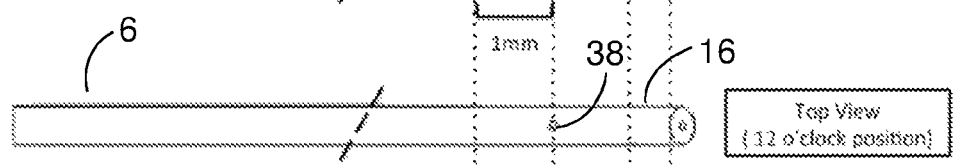
Figure 6C:
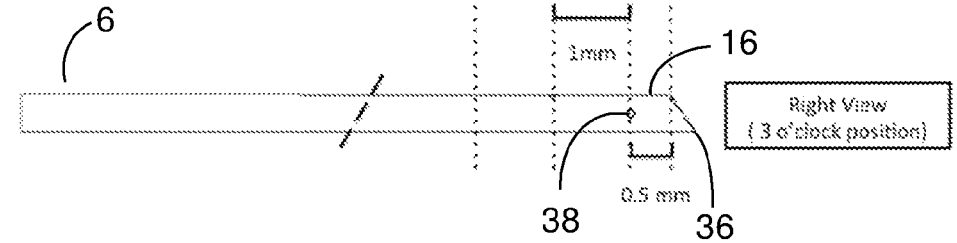

FIG. 6A-FIG. 6C illustrate different views of a tube 6 in accordance with an embodiment of the present disclosure, wherein the tube 6 comprises micro-holes 38. In some embodiments, the tube 6 can comprise one or more micro-holes 38.

FIG. 6A illustrates a left view (e.g., 9 o'clock position) of the tube 6. FIG. 6B illustrates a top view of the tube 6 (e.g., 12 o'clock position). FIG. 6C illustrates a right view (e.g., 3 o'clock position) of the tube 6.

In some embodiments, the one or more micro-holes 38 can comprise a diameter that is the same or substantially the same as the inner diameter of the tube 6. In some embodiments, two or more micro-holes 38 can be along the same axis along the tube 6 length at about the 12 o'clock position, 3 o'clock position and/or 9 o'clock position. In some embodiments, the two or more micro-holes 38 can be staggered along the tube 6 length at about the 12 o'clock position, 3 o'clock position and/or 9 o'clock position.

In some embodiments, the one or more micro-holes 38 can comprise a diameter of about 0.3 mm. In some embodiments, the tube 6 can comprise a micro-hole 38 at the 12 o'clock position of the tube 6, a micro-hole 38 at the 3 o'clock position of the tube 6, and/or a micro-hole 38 at the 9 o'clock position along the tube 6. In some embodiments, where there is more than one micro-hole 38, the micro-holes 38 can be along the same axis of the tube 6 length. In some embodiments, where there is more than one micro-hole 38, the micro-holes 38 can be staggered along the tube 6 length.

In some embodiments, the one or more micro-holes 38 can comprise a diameter of about 0.1 mm. In some embodiments, the tube 6 can comprise a micro-hole 38 at the 12 o'clock position of the tube 6, a micro-hole 38 at the 3 o'clock position of the tube 6, and/or a micro-hole 38 at the 9 o'clock position along the tube 6. In some embodiments, where there is more than one micro-hole 38, the micro-holes 38 can be along the same axis of the tube 6 length. In some embodiments, where there is more than one micro-hole 38, the micro-holes 38 can be staggered along the tube 6 length.

In some embodiments, the tube 6 can comprise a micro-hole 38 at the 12 o'clock position of the tube 6, a micro-hole 38 at the 3 o'clock position of the tube 6, and a micro-hole 38 at the 9 o'clock position along the tube 6. In some embodiments, the micro-holes 38 can be along the same axis of the tube 6 length. In some embodiments, the micro-holes 38 can be staggered along the tube 6 length.

In some embodiments, there is no micro-hole 38 at the 6 o'clock position of the tube 6 as the 6 o'clock position is typically directly above the iris of the eye. This prevents the iris from being pressed against and/or sucked into a micro-hole, and any subsequent damage therefrom.

The design of a plate 4 and/or tube 6 of the present disclosure can reduce the failure rate associated with presently available glaucoma drainage devices (GDDs) and/or reduce post-operative complications associated with presently available GDDs. Further, the design of the plate 4 and/or tube 6 can allow for easier implantation and/or deployment.

The present disclosure also relates to a stability system or fluid flow control system. In accordance with an embodiment of the present disclosure, the stability system can comprise a plate 4 of a GDD 2 (the GDD 2 comprises the plate 4 and a tube 6) plus a material comprising collagen (e.g., pericardium, pericardial tissue and/or donor sclera) applied over and/or around the plate 4 and/or a viscoelastic substance (e.g., sodium hyaluronate and/or a cross-linked hyaluronic acid) applied over and/or around the plate 4. The combination of the plate 4 with the material comprising collagen applied over and/or around the plate 4, and/or with the viscoelastic substance applied over and/or around the plate 4 can provide a fluid flow control mechanism that can prevent hypotony that can occur immediately after surgical implantation and/or can prevent raised IOP that can occur in the long-term. In some embodiments, the plate 4 can comprise a reservoir 8.

The plate 4 of the GDD 2 plus the material comprising collagen applied over and/or around the plate and/or the viscoelastic substance applied over and/or around the plate can work together to control the fluid that exits the eye thereby providing better fluid control in the long-term. The fluid flow control of a GDD 2 can be enhanced when the material comprising collagen is applied over and/or around the plate 4 of the GDD 2 and/or the viscoelastic substance is applied over and/or around the plate 4 of the GDD 2.

In some embodiments, the stability system can comprise a plate 4 of a GDD 2 and a material comprising collagen applied over and/or around the plate 4. In some embodiments, the stability system can comprise a plate 4 of a GDD 2 and a viscoelastic substance applied over and/or around the plate 4. In some embodiments, the stability system can comprise a plate 4 of a GDD 2 plus a material comprising collagen applied over and/or around the plate 4 or a viscoelastic substance applied over and/or around the plate 4. In some embodiments, the stability system can comprise a plate 4 of a GDD 2 plus a material comprising collagen applied over and/or around the plate 4 and a viscoelastic substance applied over and/or around the plate 4. In some embodiments, the material comprising collagen can be flexible. In some embodiments, the material comprising collagen can be freeze-dried. In some embodiments, the material comprising collagen can comprise a patch. In some embodiments, the viscoelastic substance can comprise an inert viscoelastic substance.

In accordance with an embodiment of the present disclosure, the stability system can comprise a plate 4 comprising a reservoir 8 plus a material comprising collagen (e.g., pericardium, pericardial tissue and/or donor sclera) applied over the reservoir 8 and/or around the plate 4 and/or a viscoelastic substance (e.g., sodium hyaluronate and/or a cross-linked hyaluronic acid) applied over the reservoir 8 and/or around the plate 4. The combination of the plate 4 with the material comprising collagen and/or with the viscoelastic substance provides a fluid flow control mechanism that can prevent hypotony that can occur immediately after surgical implantation and/or prevent raised IOP that can occur in the long-term.

Figure 7A:
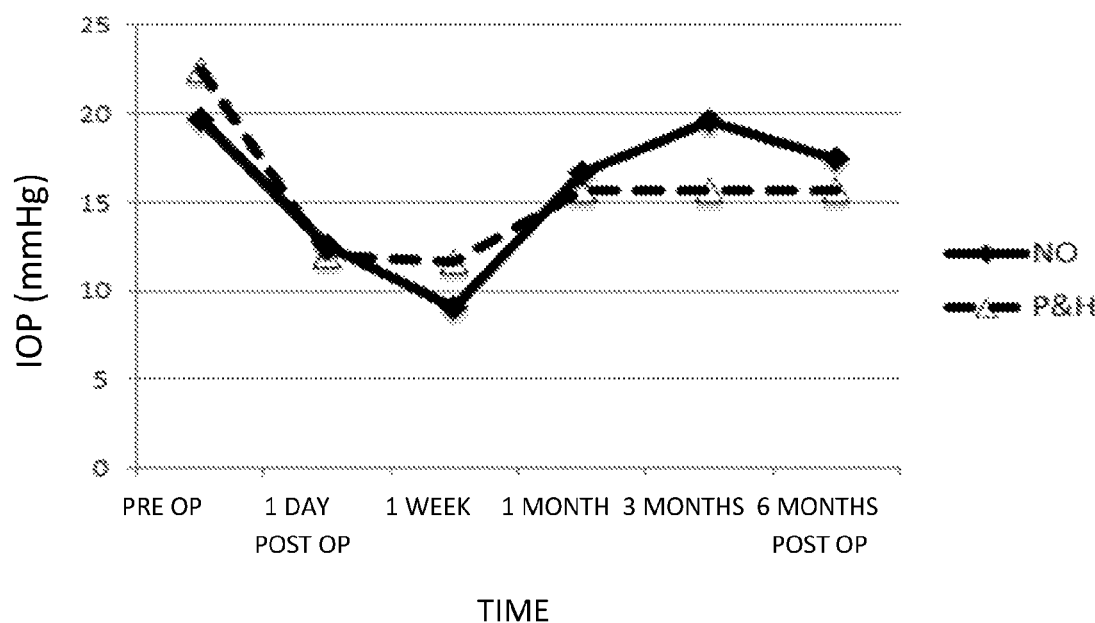
FIG. 7A-FIG. 7B show the results of a clinical study comparing the use of a modified presently available glaucoma drainage device implant (modified to include a bovine pericardial tissue (e.g., Tutopatch)) and a cross-linked hyaluronic acid (e.g., Healaflow)) with the use of an unmodified presently available glaucoma drainage device implant used as a control. In particular.
Figure 7B:
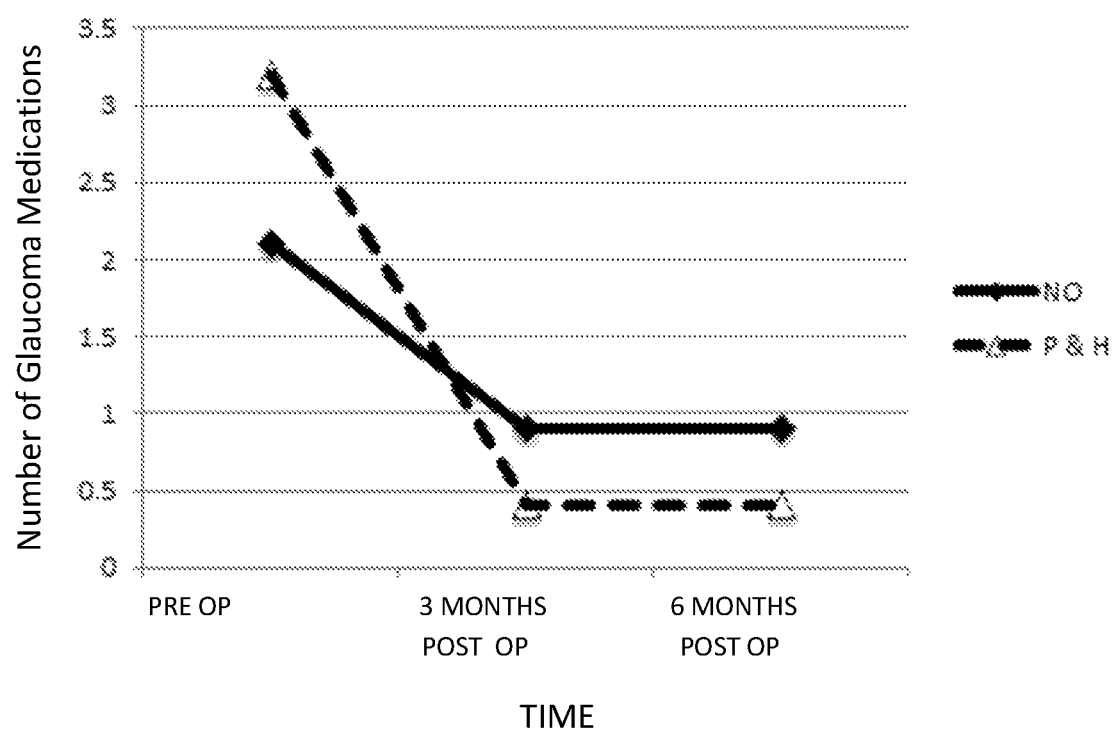

FIG. 7A-FIG. 7B and Table 1 show the results of a clinical study or clinical case series comparing the use of a modified presently available glaucoma drainage device implant (modified to include a bovine pericardial tissue/pericardial patch (e.g., Tutopatch) placed on top of the plate and a cross-linked hyaluronic acid (e.g., Healaflow) injected over the plate-tutopatch complex and on both sides of the plate) with the use of an unmodified presently available glaucoma drainage device implant as a control.

A person having ordinary skill in the art will understand that a material similar, substantially similar, equivalent, substantially equivalent or analagous to Tutopatch could have been used for the clinical study to achieve similar or substantially similar results. Also, a person having ordinary skill in the art will understand that a material similar, substantially similar, equivalent, substantially equivalent or analagous to Healaflow could have been used for the clinical study to achieve similar or substantially similar results. Further, the presently available glaucoma drainage device used in the clinical study was an Ahmed drainage device. However, a person having ordinary skill in the art will understand that other presently available drainage devices could have been used.

The clinical study or clinical case series was conducted using thirty (30) human patients. The patients were reviewed for raised IOP and hypotony prior to surgical implantation, at one (1) day post-surgical implantation, one (1) week post-surgical implantation, one (1) month post-surgical implantation, three (3) months post-surgical implantation and six (6) months post-surgical implantation. The IOP of the patients was monitored to ascertain whether or not hypotony and/or late stage raised IOP occurred. The primary outcome measures were as follows: (1) success and failure based on the mean intraocular pressure (IOP); (2) the occurrence of the hypertensive phase, defined as IOP>21 mmHg; (3) the occurrence of ocular hypotony, defined as IOP<6 mmHg; and (4) the number of post-operative anti-glaucoma medications (e.g., anti-glaucoma eye drops) required.

In patients that were treated with the modified presently available glaucoma drainage device comprising the bovine pericardial tissue/pericardial patch (e.g., Tutopatch) and cross-linked hyaluronic acid (e.g., Healaflow), six months after surgery the IOP ($15.6 \pm 4.2$ mmHg) and number of anti-glaucoma medicines ($0.4 \pm 1.0$) used were significantly lower when compared to pre-operative values (IOP=$22.5 \pm 12.3$ mmHg, p=0.026; number of anti-glaucoma medicines=$3.2 \pm 1.2$, p<0.001). The success rate of the modified presently available glaucoma drainage device with the Tutopatch and Healaflow at 6 months after surgery was 95.2%. A hypertensive phase occurred in 16% of the operated eyes between one to three months after the surgery with an IOP range of 22-26 mmHg.

In the control group or control eyes of patients treated with the unmodified presently available glaucoma drainage device that did not include a Tutopatch and Healaflow, the mean IOP was $17.4 \pm 5.1$ mmHg 6 months after surgery. The number of anti-glaucoma medicines used decreased from $2.10 \pm 1.5$ to $0.9 \pm 0.9$ (p=0.01, Student's t-test) 6 months after surgery. The success rate of the unmodified presently available glaucoma drainage device that did not include the Tutopatch and Healaflow at 6 months after surgery or implantation was 70%. 50% of the control eyes had an IOP range of 25-43 mmHg during a hypertensive phase noted at 1-3 months after surgery.

FIG. 7A shows the IOP trend of all patient/subject eyes from an experimental group (the group treated with the modified presently available glaucoma drainage device implant having the Tutopatch and Healaflow) and all patient/subject eyes from a control group (the group treated with the unmodified presently available glaucoma drainage device implant without the Tutopatch and Healaflow) before and after surgery with 6 months of follow up. The broken line with open triangles represents the IOP trend of the experimental group with the Tutopatch and Healaflow. The solid line with diamonds represents the IOP trend of the control group without the Tutopatch and healaflow.

FIG. 7A clearly shows that the mean IOP of the experimental group (having a modified presently available glaucoma drainage device implant comprising a Tutopatch and Healaflow) at 1 month post-surgical implantation, 3 months post-surgical implantation and 6 months post-surgical implantation follows a straight, flat line showing a stable and lower IOP level compared to the control group (having an unmodified presently available glaucoma drainage device implant without the Tutopatch and Healaflow).

FIG. 7B shows the number of anti-glaucoma medications required by the experimental group (having a modified presently available glaucoma drainage device implant comprising a Tutopatch and Healaflow) and the number of anti-glaucoma medications required by the control group (having an unmodified presently available glaucoma drainage device implant without the Tutopatch and Healaflow) before and after surgery with 6 months of follow up. The broken line with open triangles represents the number of anti-glaucoma medications required by the experimental group with the Tutopatch and Healaflow. The solid line with diamonds represents the number of anti-glaucoma medications required by the control group without the Tutopatch and healaflow.

As shown in FIG. 7A-FIG. 7B and Table 1 below, the use of a material comprising collagen (e.g., bovine pericardial tissue/pericardial patch) and the use of a viscoelastic substance (e.g., a cross-linked hyaluronic acid) improved the outcome of glaucoma drainage device implant surgery. The use of the material comprising collagen and the use of the viscoelastic substance resulted in a significantly lower IOP, a significantly lower number of anti-glaucoma medicines and a significantly lower rate of hypertensive phase occurrence.

TABLE 1

The results of the clinical study or clinical case series comparing the use of the modified presently available glaucoma drainage device implant (modified to include a bovine pericardial tissue/pericardial patch (Tutopatch) placed on top of the plate and cross-linked hyaluronic acid (Healaflow) injected over the plate-Tutopatch complex and on both sides of the plate) with the use of the unmodified presently available glaucoma drainage device implant as a control.

|  | MODIFIED GDD WITH TUTOPATCH + HEALAFLOW | CONTROL UNMODIFIED GDD WITH NO TUTOPATCH AND NO HEALAFLOW |
|---|---|---|
| NO. of PRE-OP ANTI-GLAUCOMA MEDICINES | $3.2 \pm 1.2$ | $2.10 \pm 1.5$ |
| NO. of POST-OP ANTI-GLAUCOMA MEDICINES | $0.4 \pm 1.0$ | $0.9 \pm 0.9$ |
| HYPERTENSIVE PHASE | 16% (IOP 22-26 mm Hg) | 50% (IOP 25-43 mm Hg) |
| SUCCESS RATE AT 6 MONTHS AFTER SURGERY: | 95.2% | 70% |

The clinical study or clinical case series showed that the use of a material comprising collagen (e.g., pericardium, pericardial tissue, donor sclera and/or pericardial patch) and viscoelastic substance (e.g., sodium hyaluronate and/or a cross-linked hyaluronic acid) with glaucoma drainage devices resulted in increased stability in IOP post-surgical implantation thereby reducing the incidence of ocular raised IOP and ocular hypotony.

Method of Manufacturing a Glaucoma Drainage Device of the Present Disclosure

The present disclosure also relates to a method of manufacturing a glaucoma drainage device (GDD) 2 described above.

In accordance with an embodiment of the present disclosure, a plate 4 can be manufactured by: providing a medical grade elastomer material (e.g., medical grade silicone); and moulding the medical grade elastomer material to form the plate 4. The plate 4 comprising the moulded medical grade elastomer material can then be polished to provide a smooth surface. The plate 4 can be formed to include a tube retaining structure 20, tube receiving hole 30, tube receiving channel 30', reservoir 8, one or more plate channels 10, one or more fenestrations 32, and/or one or more suture holes 34.

In accordance with an embodiment of the present disclosure, a tube 6 can be manufactured by: providing a medical grade elastomer material (e.g., medical grade silicone) and extruding the medical grade elastomer material to form the tube 6. Laser cutting can be used to create a bevelled edge 36 at the distal end 16/inlet end 16/inflow end 16 of the tube 6. Laser drilling can be used to form one or more microholes along the length or side of the tube 6.

In some embodiments, a method of manufacturing a tube 6 can comprise: providing a medical grade elastomer material; extruding the medical grade elastomer material to form a tube 6; laser cutting the distal end 16 or inlet end 16 of the tube 6 to form a beveled edge 36 at the distal end 16 or inlet end 16 of the tube 6; and/or forming one or more microholes 38 along the length or side of the tube 6 by laser drilling.

In some embodiments, a method of manufacturing a tube 6 can comprise: providing a medical grade elastomer material; and moulding the medical grade elastomer material to form a tube 6 having a beveled edge 36 at the distal end 16 or inlet end 16 and/or having one or more micro-holes 38 along the length or side of the tube 6.

In some embodiments, a method of manufacturing a tube 6 can comprise: providing a medical grade elastomer material; moulding the medical grade elastomer material to form a tube 6 having a beveled edge 36; and forming one or more micro-holes 38 along the length or side of the tube 6 via laser drilling.

In accordance with an embodiment of the present disclosure, a biodegradable cuff 18 can be manufactured by: providing a material comprising PDLGA, PLGA, a biodegradable polymer, a biocompatible polymer or a combination of one or more thereof; and extruding the material to form a cuff 18 or cuff tube 18.

In accordance with an embodiment of the present disclosure, a glaucoma drainage device (GDD) 2 can be manufactured by: providing or manufacturing a plate 4 and a tube 6; and assembling the plate 4 to the tube 6. In some embodiments, the plate 4 and the tube 6 can be assembled by threading the tube 6 through a tube receiving hole 30 and tube receiving channel 30' of the plate 4 by hand. In some embodiments, the plate 4 and the tube 6 can be assembled by threading the tube 6 through the tube receiving hole 30 and tube receiving channel 30' of the plate 4 utilizing an automated device/automated apparatus. In some embodiments, the plate 4 can be over-moulded onto the tube 6.

In accordance with an embodiment of the present disclosure, a cuff 18 and a tube 6 can be manufactured as separate components. In some embodiments, the cuff 18 and the tube 6 can be pre-cut to the desired length. In some embodiments, the tube 6 can be threaded through the cuff 18 by hand. In some embodiments, the tube 6 can be threaded through the cuff 18 utilizing an automated device/automated apparatus.

Method of Implanting a Glaucoma Drainage Device of the Present Disclosure

The present disclosure also relates to a method of implanting a glaucoma drainage device (GDD) 2 described above in a patient or subject.

In accordance with an embodiment of the present disclosure, a clinician can dissect a sub-Tenon's/subconjuctival pocket that is about the size of the plate 4 of the GDD 2. A material comprising collagen can be placed on top of the plate 4 and/or around the plate 4 to form a plate-collagen complex prior to insertion of the plate-collagen complex. In some embodiments, the material comprising collagen can comprise pericardium, pericardial tissue and/or donor sclera. In some embodiments, the material comprising collagen can be flexible. In some embodiments, the material comprising collagen can comprise a patch.

The plate 4 can be adapted to be placed over the sclera of the eye. The plate 4 can comprise a shape and/or size that allows for easier implantation of the plate 4 and GDD 2.

The tube 6 of the GDD 2 can comprise a proximal end 14/outflow end 14 that is removably connected to the plate 4. The tube 6 can also comprise a distal end 16/inlet end 16/inflow end 16 extending away from the plate 4, wherein the distal end 16/inlet end 16/inflow end 16 comprises a length that is long enough to extend into the anterior chamber of the eye. The distal end 16/inlet end 16/inflow end 16 is the end that is inserted into the eye. The surgeon or clinician can insert the tube 6 through an incision that is made into the eye. The tube 6 can comprise a bevelled edge 36 at the distal end 16/inlet end 16/inflow end 16 of the tube 6, wherein the bevelled edge 36 aids in the insertion of the tube 6.

Post-insertion of the tube 6 into the eye, the tube 6 can be pulled from either end of the tube retaining structure 20 (e.g., via the proximal end 14/outflow end 14 of the tube 6 that is proximal to the tube retaining structure 20; and/or via the section of the tube 6 just distal to the tube retaining structure 20 which is not in the anterior chamber of the eye) and adjusted to the suitable length for the patient's eye. The tube 6 can be cut from the proximal end 14/outflow end 14 closer to the plate 4 thereby eliminating the need for the surgeon or clinician to take the tube 6 out of the eye to cut the tube 6 to the appropriate length. This can also result in maintaining a smooth profile of the tube 6 at the distal end 16/inlet end 16/inflow end 16 that enters the eye.

The cuff 18 functioning as a flow restrictor on the tube 6 and the GDD 2 can eliminate the extra step of having to create a temporary flow restriction by using a suture knot. The extra step of creating a temporary flow restriction using a suture knot is common when using presently available non-valved glaucoma drainage devices.

The plate 4 can be secured into position on the sclera via one or more suture holes 34 about 8.5 mm posterior to the limbus.

Prior to closing the sub-conjuctiva/sub-Tenon's pocket, an inert viscoelastic substance (e.g., a cross-linked hyaluronic acid) can be injected on top of the plate-collagen complex and/or around the plate 4. The combination of the plate 4 of the GDD 2 with the material comprising collagen over and/or around the plate 4, and/or with the viscoelastic substance over and/or around the plate 4 can function as a stability system. The stability system comprising the plate 4 with the material comprising collagen over and/or around the plate 4, and/or with the inert viscoelastic substance over and/or around the plate 4 can aid in fluid flow control.

FIGS. 8A-8H and Table 2 show bench data results of gravity flow simulations comparing the use of a representative glaucoma drainage device (GDD) 2 in accordance with the present disclosure with the use of a modified commercially available Baerveldt device. In the modified Baerveldt device, a 200 micron suture was incorporated or formed in the tube thereof to decrease the diameter of the tube, and therefore increase the resistance of fluid flow within/through the tube. This modification is sometimes applied in clinical practice. The gravity flow simulates the situation when the eye has an initially high pressure of >21 mmHg. A pressure differential results in the draining of the fluid from the eye.

Figure 8A:
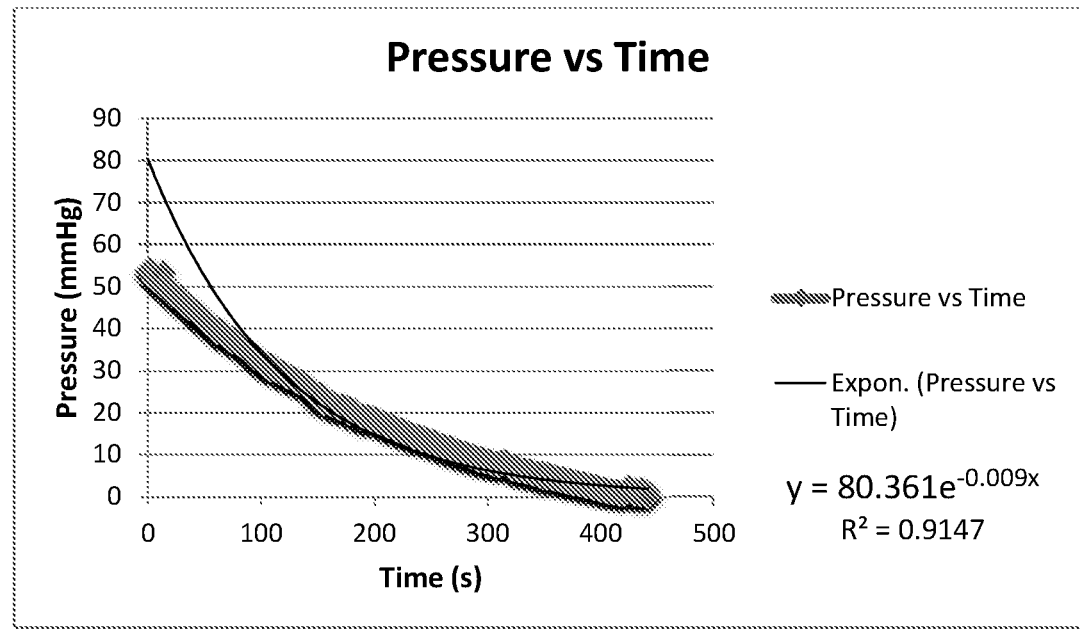
FIG. 8A-8H show bench data results of gravity flow simulations comparing the use of a glaucoma drainage device (GDD) 2 in accordance with the present disclosure with the use of a modified Baerveldt device having a 200 micron suture formed in a tube thereof. More particularly, FIGS. 8A and 8C respectively show a first and a second set of simulated eye pressure drop trends versus time, as fluid is drained through the modified Baerveldt device.
Figure 8B:
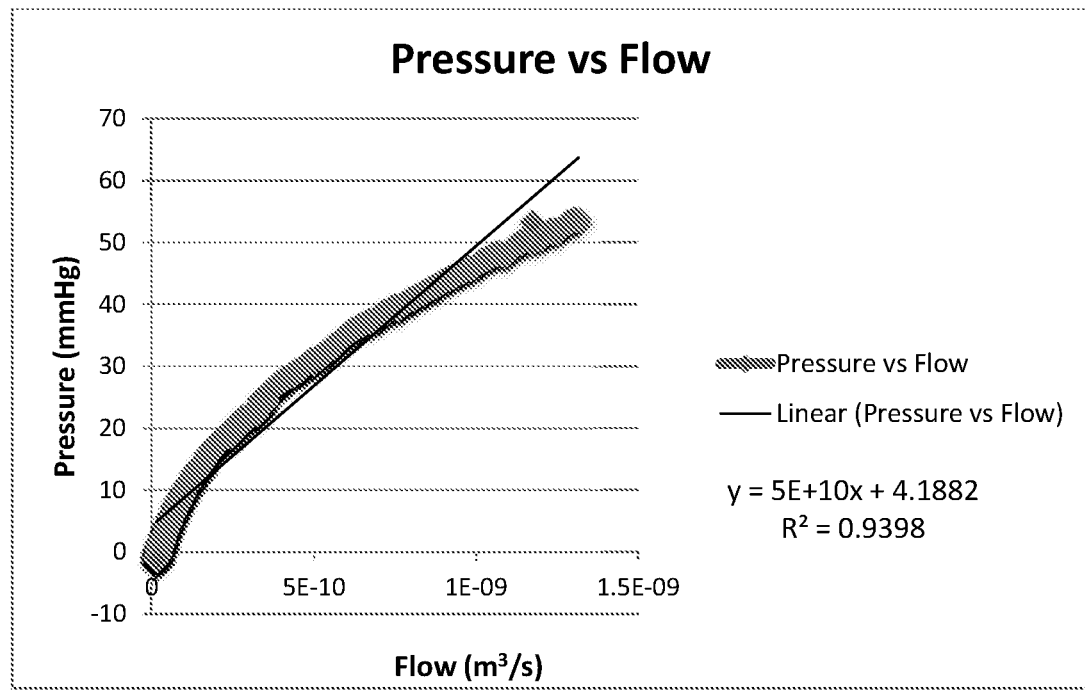
Figure 8C:
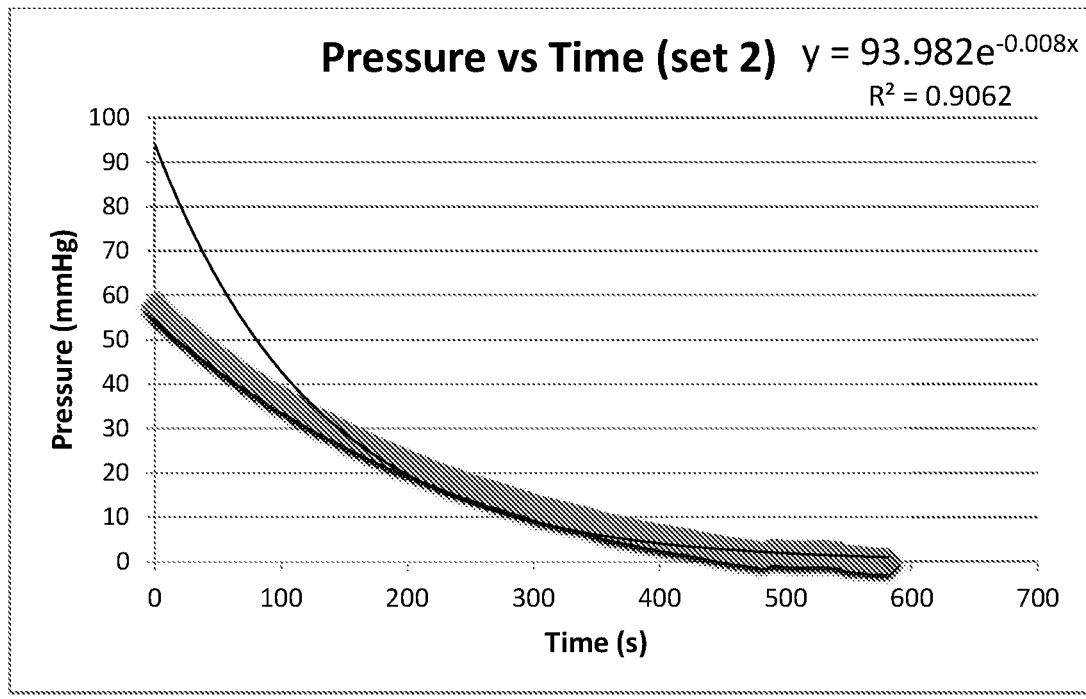

FIGS. 8A and 8C respectively show a first and a second set of simulated eye pressure drop trends versus time, as fluid is drained through the modified Baerveldt device. The broken line with diamonds represents the simulated eye pressure trend, and the solid line represents an exponential curve fitted to the simulated data.

Figure 8D:
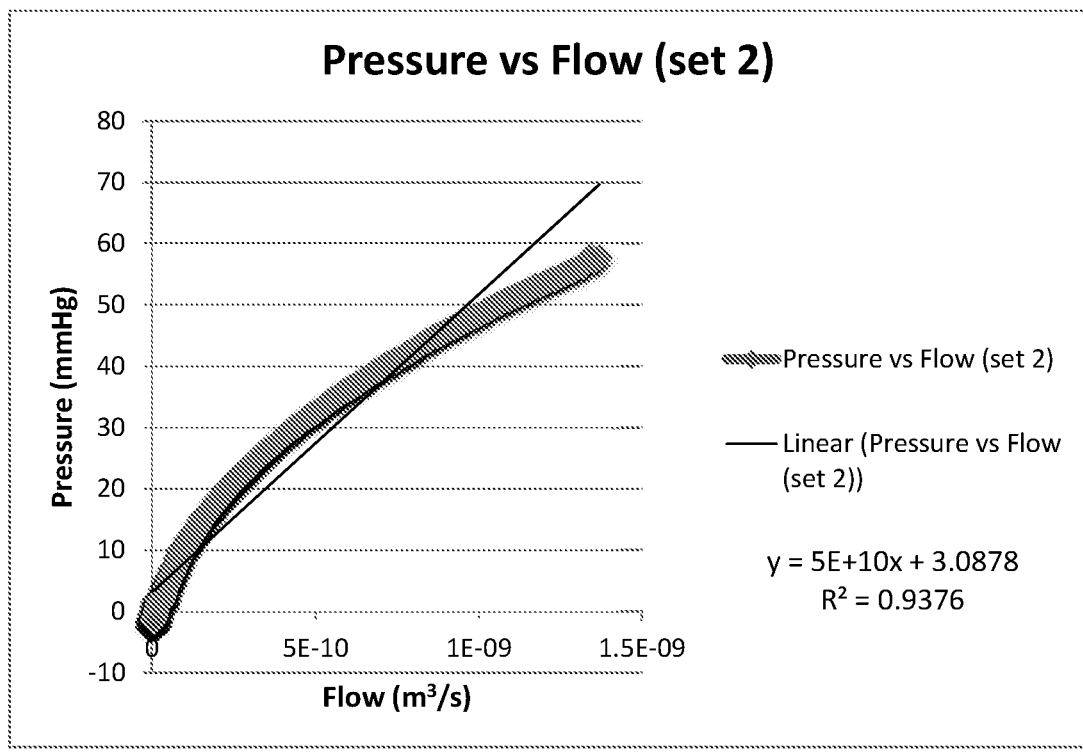

FIGS. 8B and 8D respectively show a first and a second set of simulated eye pressure versus flow trends, indicating a mathematical relationship (e.g., corresponding to a relationship based on or derivable using the Poiseuille equation) between pressure and fluid flow through the modified Baerveldt device. The broken line with diamonds represents the simulated pressure versus flow trend. The solid line represents a linear line fitted to the simulated data. The slope of the fitted linear line defines a resistance of the device to fluid flow within/through its tube. Hence, the resistance of the modified Baerveldt device is approximately $5 \times 10^{10}$ (mmHg/(m$^3$/s)), reading from both FIGS. 8B and 8D.

Figure 8E:
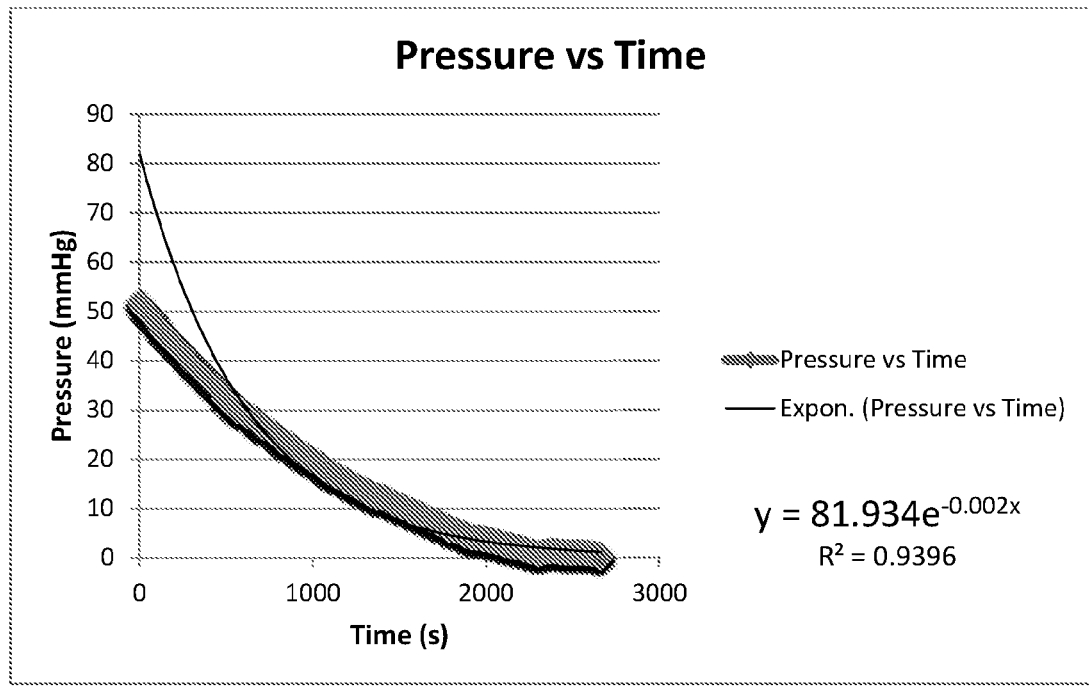
Figure 8F:
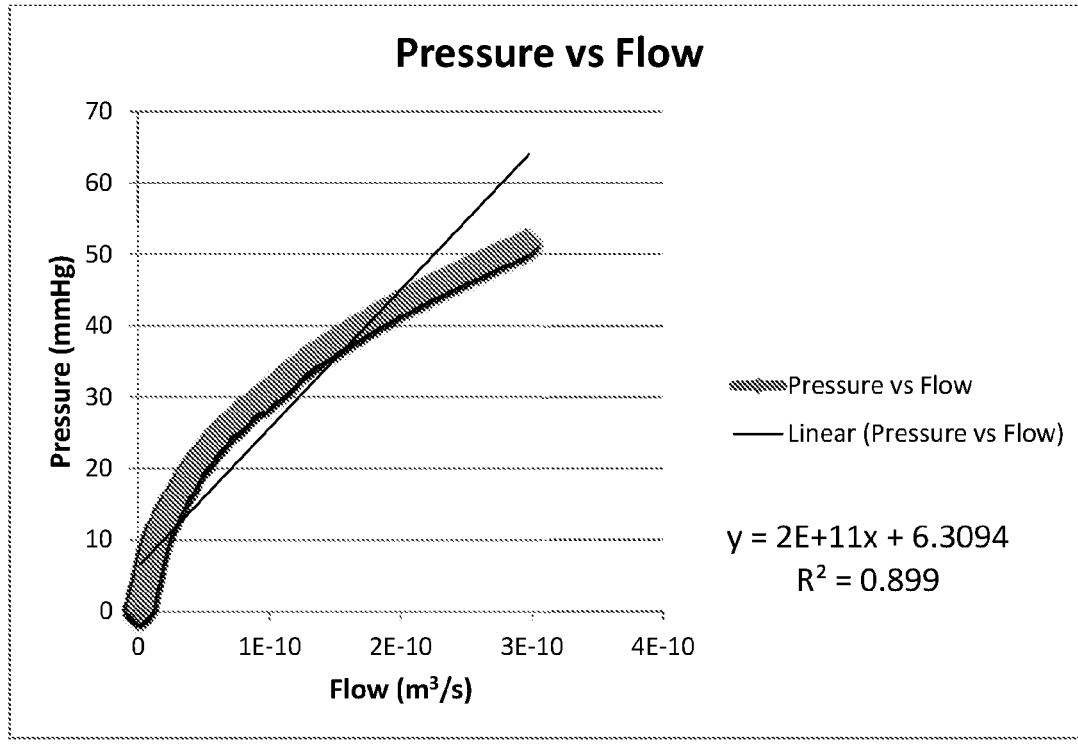
Figure 8G:
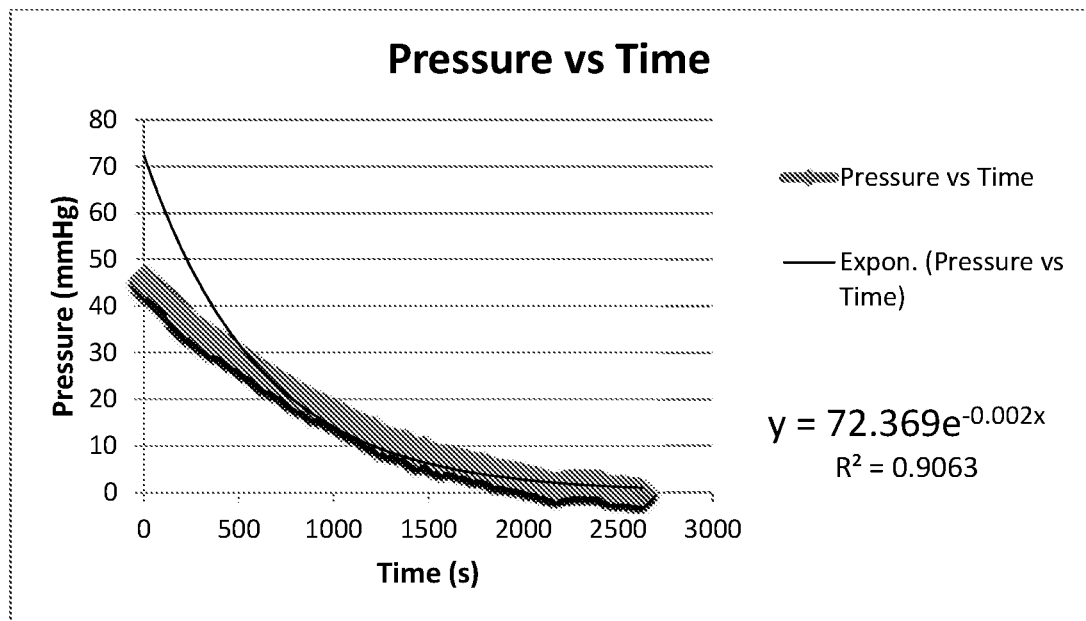

FIGS. 8E and 8G respectively show a first and a second set of simulated eye pressure drop trends versus time, using a glaucoma drainage device (GDD) 2 in accordance with the present disclosure. The broken line with diamonds represents the simulated eye pressure drop trend, and the solid line represents an exponential curve fitted to the simulated data.

Figure 8H:
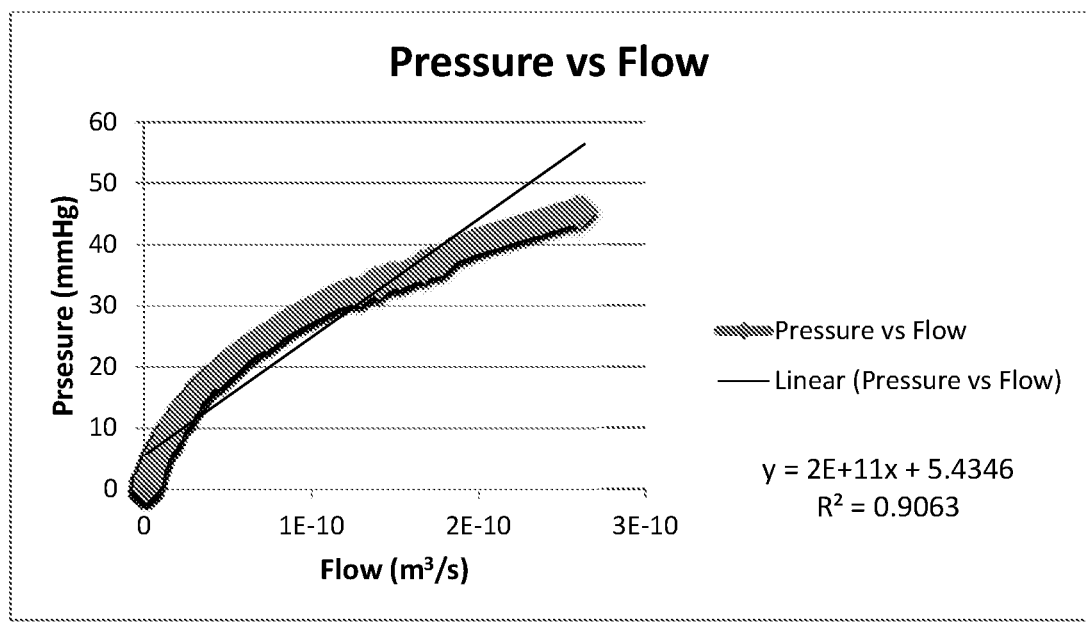

FIGS. 8F and 8H respectively show a first and a second set of simulated eye pressure versus flow trends, indicating a mathematical relationship (e.g., corresponding to a relationship based on or derivable using the Poiseuille equation) between pressure and fluid flow through the glaucoma drainage device (GDD) 2 in accordance with the present disclosure. The broken line with diamonds represents the simulated eye pressure trend. The solid line represents a linear curve fitted to the simulated data. The slope of the fitted linear line defines a resistance of the device to fluid flow within through its tube. Hence, the resistance of this glaucoma drainage device (GDD) 2 in accordance with the present disclosure is approximately $2 \times 10^{11}$ (mmHg/(m$^3$/s)), reading from both FIGS. 8F and 8H.

Table 2 below summarizes the average resistance of the modified Baerveldt device and the average resistance of the glaucoma drainage device (GDD) 2 in accordance with the present disclosure, as calculated from gravity flow simulation. In Table 2, "System R" refers to experimental measurement results obtained using the experimental setup (e.g., tubes, t-connectors, etc. . . . ) without having the modified Baerveldt device or the glaucoma drainage device (GDD) 2 in accordance with the present disclosure fluidically coupled to the experimental setup. The results show that the glaucoma drainage device (GDD) 2 in accordance with the present disclosure exhibits or produces higher resistance than the modified Baerveldt device. A higher resistance reduces the rate at which fluid flows out of the aqueous chamber of the eye. This may prevent immediate post-operative hypotony when the intraocular pressures in the eye are initially high.

TABLE 2

Average resistance (mmHg/(m$^3$/s)) of a modified Baerveldt device (MBD) and a glaucoma drainage device (GDD) 2 in accordance with the present disclosure, calculated from gravity flow simulation.

| Resistance | Average (system + device) | System R | Average R |
|---|---|---|---|
| MBD | $5 \times 10^{10}$ | $2.5 \times 10^9$ | $4.75 \times 10^{10}$ |
| GDD | $2 \times 10^{11}$ | $4 \times 10^9$ | $1.96 \times 10^{11}$ |

FIGS. 9A-9D and Table 3A-3C show bench data results of constant flow simulations comparing the use of a glaucoma drainage device (GDD) 2 in accordance with the present disclosure with the use of a modified commercially available Baerveldt device having a 200 micron suture included in the tube thereof, in a manner identical or essentially identical to that set forth above. With respect to the results shown in FIGS. 9A-9D and Tables 3A-3C, pressures were zeroed prior to experiment initiation. The constant flow simulates the situation after initial drainage from high pressures, and the eye reaching a stabilization pressure between about 15-20 mmHg. The eye continues to produce about 2 µl/min of fluid, which is simulated by the fluid pump, while fluid continually drains out through the device to maintain eye pressure between 15-20 mmHg.

Figure 9A:
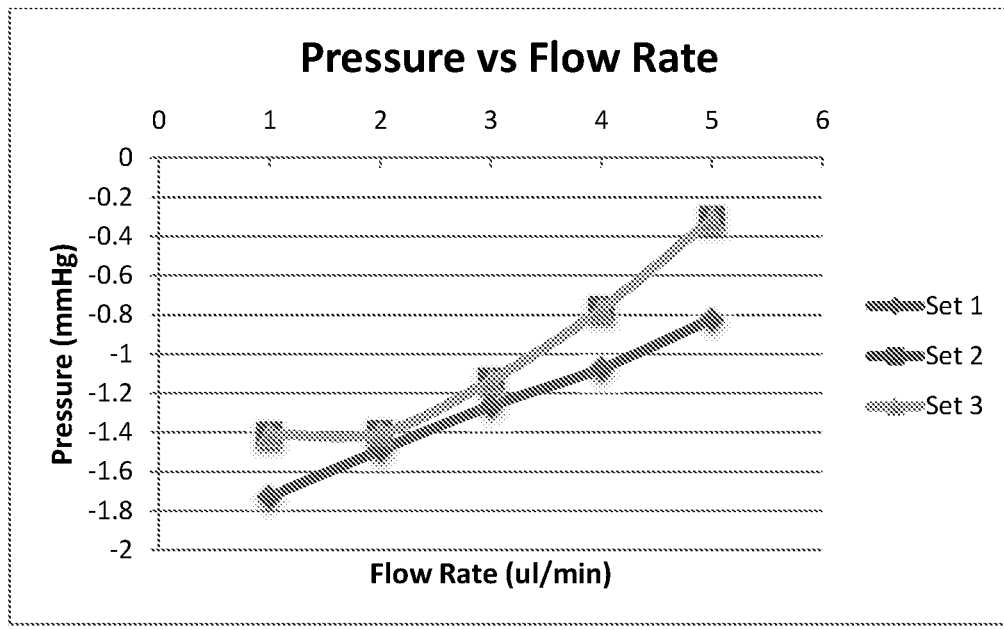
FIG. 9A-9D show bench data results of constant flow simulations comparing the use of a glaucoma drainage device (GDD) 2 in accordance with the present disclosure with the use of a modified Baerveldt device having a 200 micron suture formed in a tube thereof. More particularly.
Figure 9B:
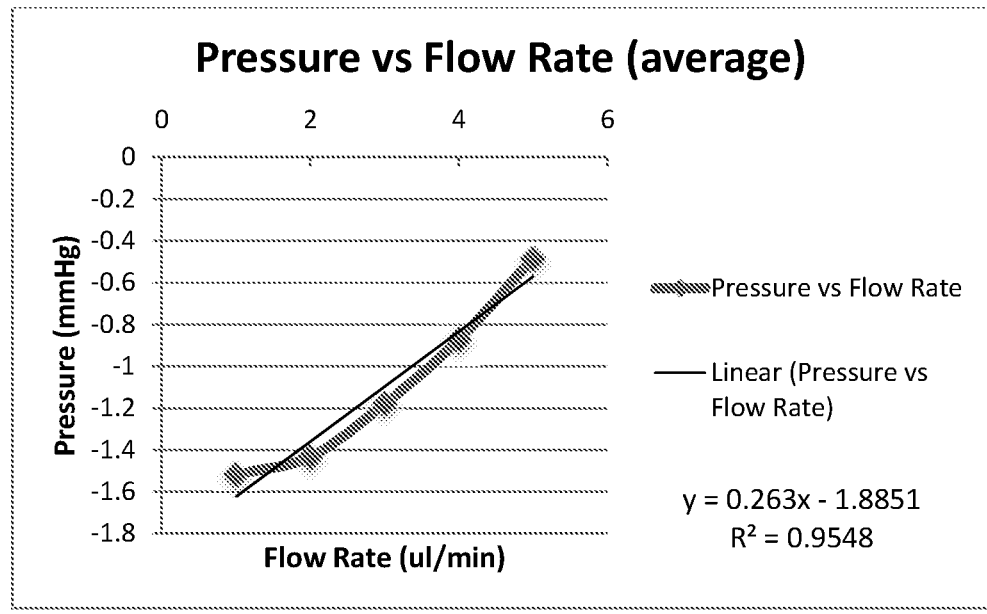

FIG. 9A and Table 3A shows three sets of simulated eye pressure versus flow trends, using the modified Baerveldt device with a 200 micron suture included in its tube. In FIG. 9A, the broken line with diamonds, squares, and triangles respectively represent the first, second, and third set of simulated eye pressure versus flow trends. The broken line with diamonds in FIG. 9B represents the average of the three sets of simulated eye pressure versus flow results of FIG. 9A. The solid line in FIG. 9B represents a linear line fitted to the average of the simulated data. The slope of the fitted linear line gives the resistance of the device. Hence, the resistance of the modified Baerveldt device is approximately 0.263 (mmHg/(µl/min)), as read from FIG. 9B.

TABLE 3A

Results of three sets of simulated eye pressure (mmHg) at different flow rates (µl/min) under constant flow simulation, using the modified Baerveldt device with a 200 micron suture included in its tube.

| Flow Rate | set 1 | 2 | 3 | Average |
|---|---|---|---|---|
| 1 | −1.727699557 | −1.41047196 | −1.41047196 | −1.516214492 |
| 2 | −1.491226415 | −1.402491676 | −1.402491676 | −1.432069922 |
| 3 | −1.265882353 | −1.135077691 | −1.135077691 | −1.178679245 |
| 4 | −1.074108828 | −0.770976693 | −0.770976693 | −0.872020738 |
| 5 | −0.822609661 | −0.310510544 | −0.310510544 | −0.48121025 |

Figure 9C:
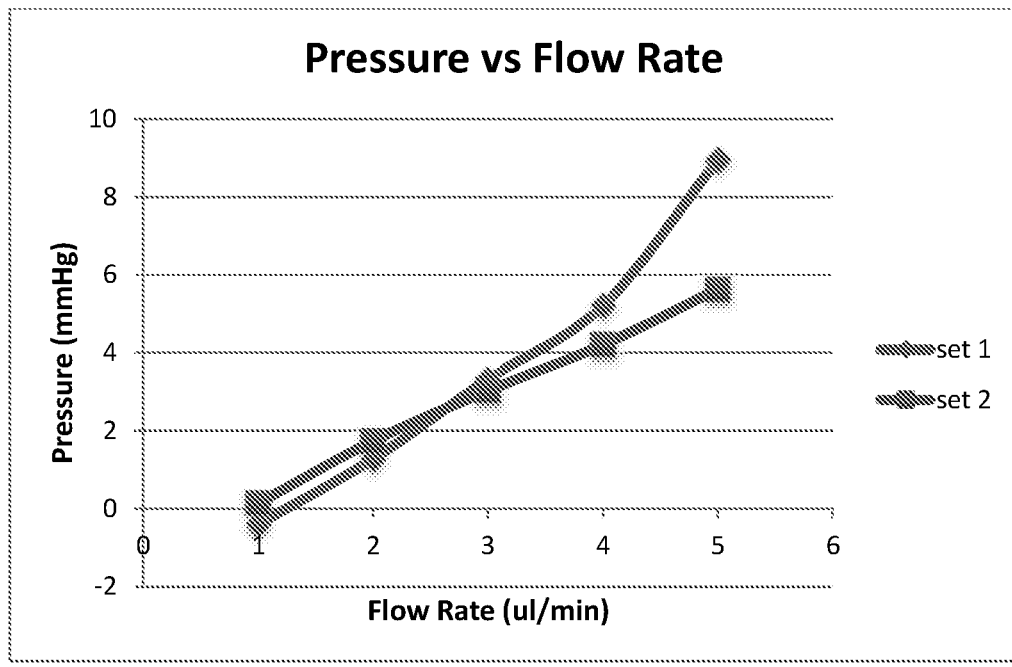
Figure 9D:
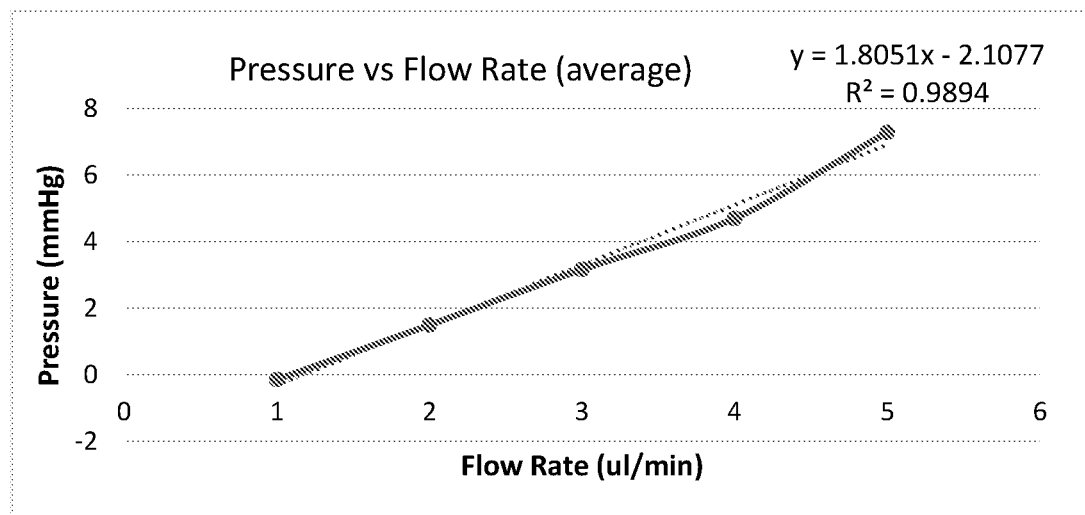

FIG. 9C and Table 3B show two sets of simulated eye pressure versus flow trends, using the glaucoma drainage device (GDD) 2 in accordance with the present disclosure. In FIG. 9C, the broken line with diamonds and squares respectively represent the first and second set of simulated eye pressure versus flow trends. The broken line with circles in FIG. 9D represents the average of the two sets of simulated eye pressure versus flow results of FIG. 9C. The solid dashed line in FIG. 9D represents a linear line fitted to the average of the simulated data. The slope of the fitted linear line gives the resistance of the device. Hence, the resistance of the glaucoma drainage device (GDD) 2 in accordance with the present disclosure is approximately 1.8051 (mmHg/(μl/min)), as read from FIG. 9D.

TABLE 3B

Results of two sets of simulated eye pressures (mmHg) at different flow rates (μl/min) under constant flow simulation, using a glaucoma drainage device (GDD) 2 in accordance with the present disclosure.

| Flow Rate | Set 1 | Set 2 | Average |
|---|---|---|---|
| 1 | −0.404350721 | 0.135480289 | −0.134435216 |
| 2 | 1.273409217 | 1.734497501 | 1.503953359 |
| 3 | 3.322685905 | 3.020971682 | 3.171828793 |
| 4 | 5.211183036 | 4.202880133 | 4.707031584 |
| 5 | 8.953396226 | 5.625654828 | 7.289525527 |

Table 3C below summarizes the average resistance of the modified Baerveldt device and the average resistance of the glaucoma drainage device (GDD) 2 in accordance with the present disclosure, as calculated from the constant flow simulation. In Table 3C, "System R" refers to experimental measurement results obtained using the experimental setup (e.g., tubes, t-connectors, etc. . . . ) without having the modified Baerveldt device or the glaucoma drainage device (GDD) 2 in accordance with the present disclosure fluidically coupled to the experimental setup. The results show that the glaucoma drainage device (GDD) 2 in accordance with the present disclosure produces higher resistance than the modified Baerveldt device. This may prevent post-operative hypotony that can occur after stabilization pressure is reached in the eye.

TABLE 3C

Results of the average resistance (mmHg/(ul/min)) of the modified Baerveldt device (MBD) and the glaucoma drainage device (GDD) 2 in accordance with the present disclosure, calculated from constant flow simulation.

| Resistance | Average (System + Device) | System R | Average R |
|---|---|---|---|
| MBD | 0.2630 | 0.0033 | 0.2597 |
| GDD | 1.8051 | 0.0593 | 1.7458 |

Preclinical Studies in a rabbit model have also been carried out to evaluate the in-vivo safety and technical performance of a glaucoma drainage device (GDD) 2 in accordance with the present disclosure, for the treatment of glaucoma. The glaucoma drainage device (GDD) 2 in accordance with the present disclosure has been evaluated for the following safety endpoints: biocompatibility and potential ocular irritation, post-surgical complications, and ease of implantation.

The device should have at least an equivalent safety profile when compared to commercial devices, as evaluated by post-surgical complications including inflammation, infection, device occlusion, device exposure/extrusion, corneal or lens damage, eye discharge, squinting and ocular discomfort, etc.

The GDD 2 in accordance with the present disclosure was determined to be easier to implant than current commercial devices. No inflammation or infection was observed in the animals, indicating biocompatibility of the glaucoma drainage device (GDD) 2 in accordance with the present disclosure. On enucleation, the GDD 2 is noted to be visible, with no adverse reaction observed.

Table 4 below shows the intraocular pressure (IOP) (mmHg) of animals from a control group and an experimental group. The control group is animals without implantation/use of the GDD 2, and the experimental group is animals in which the GDD 2 has been implanted and used. In Table 4, the control group includes sample No. 0637 (Control), 0638 (Control), and the experimental group includes sample No. 0637, 0638, and 0639 (where L indicates left eye, and R indicates right eye). Table 4 shows IOP results pre-operatively and at times of 1 week, 2 weeks, 6 and 12 weeks after experimental group surgery.

TABLE 4

Results of intraocular pressure (IOP)(mmHg) of the animals from a control group and an experimental group pre-operatively and at 1 week, 2 weeks, and 6 and 12 weeks after experimental group surgery.

|  | 0637 | 0638 | 0639 L | 0639 R | 0637 (Control) | 0638 (Control) |
|---|---|---|---|---|---|---|
| Pre-op | 10 | 15 | 13 | 12 | 10 | 14 |
| Week 1 | 3 | 5 | 14 | 6 | 10 | 14 |
| Week 2 | 8 | 7 | 10 | 3 | 12 | 10 |
| Week 6 | 12 | 10 | 14 | 13 | 10 | 13 |
| Week 12 | 21 | 13 | 18 | 16 | 19 | 12 |

As shown in Table 4, no persistent hypotony in the experimental group was observed after 2 weeks. Although there was low intraocular pressure (IOP) in Sample No. 0639R, images did not indicate a shallow anterior chamber. The results also show that all eyes had intraocular pressures close to physiological values. This indicates fluid is flowing in the GDD 2 across the time periods considered.

Method of Controlling Intra-Ocular Pressure

The present disclosure further relates to a method of controlling intra-ocular pressure (IOP) in a patient or subject via the use of a glaucoma drainage device (GDD) 2 described above.

In accordance with an embodiment of the present disclosure, IOP can be controlled by: providing a GDD 2; and implanting the GDD 2 in a patient or subject. The GDD 2 comprises a plate 4 and tube 6.

In some embodiments, the tube 6 can comprise a cuff 18, wherein the cuff 18 comprises a biodegradable cuff 18 or biocompatible erodible cuff 18.

In some embodiments, the cuff 18 can cause the tube 6 to be constricted to a diameter whereby the fluid flow rate through the tube 6 is about 2 μL/min thereby preventing early stage hypotony.

The cuff 18 can gradually degrade such that the constriction on the tube 6 caused by the cuff 18 decreases as the fibrous tissue over the plate 4 forms (e.g., bleb formation) thereby preventing late stage raised IOP.

In some embodiments, the cuff 18 can begin to degrade (and thereby begin to lose its mechanical strength and/or mechanical properties) not earlier than four (4) weeks after implantation thereby preventing excessive fluid drainage that can lead to hypotony in the early phase (e.g., before fibrous tissue formation over the plate 4 of the GDD 2) and not later than eight (8) weeks after implantation thereby allowing additional outflow to minimize excess fluid retention that can cause post-operative raised IOP.

In some embodiments, the cuff 18 can fully degrade and fully lose its mechanical strength and/or mechanical properties at about eight (8) weeks after implantation or after about eight (8) weeks after implantation.

In some embodiments, the plate 4 can comprise a reservoir 8, wherein the reservoir 8 holds a patch material comprising collagen (e.g., pericardium, pericardial tissue and/or donor sclera) over and/or around the plate 4 and/or an inert viscoelastic substance (e.g., sodium hyaluronate and/or a cross-linked hyaluronic acid) over and/or around the plate 4. The plate 4 of the GDD 2 with the material comprising collagen over and/or around the plate 4 and/or with the viscoelastic substance over and/or around the plate 4 can function as a stability system.

In some embodiments, the stability system can comprise a plate 4 of a GDD 2, a material comprising collagen applied over and/or around the plate 4, and a viscoelastic substance applied over and/or around the plate 4. In some embodiments, the material comprising collagen can be flexible. In some embodiments, the material comprising collagen can be freeze-dried. In some embodiments, the material comprising collagen can comprise a patch. In some embodiments, the viscoelastic substance can comprise an inert viscoelastic substance.

The reservoir 8 can allow initial fluid flow to lower eye pressure immediately. The material comprising collagen can add additional pressure on the plate 4, slowing down fluid flow to the conjunctiva and preventing over-drainage that can lead to hypotony. The material comprising collagen can also brace the conjunctiva thereby preventing artificial thickening and stretching, and aiding in bleb formation, which can prevent late stage raised IOP. The viscoelastic substance can lift and expand the conjunctiva and prevent scarring. The viscoelastic substance can also aid in bleb formation and can help to prevent late stage raised IOP.

The cuff 18 and stability system (e.g., the plate 4 plus the material comprising collagen and/or the viscoelastic substance) can be used together to control IOP or can be used independently of each other to control IOP.

Method of Preventing Complications

The present disclosure further relates to a method of preventing complications associated with presently available glaucoma drainage devices (GDDs).

In accordance with an embodiment of the present disclosure, complications associated with presently available GDDs can be prevented by: providing a glaucoma drainage device (GDD) 2 described above; and implanting the GDD 2 in a patient or subject.

The GDD 2 can have a low profile to aid in bleb formation and/or prevent stretching of the conjunctiva. Stretching and/or deformation of the conjunctiva can impede blood flow in the conjunctival capillaries leading to ischemia and subsequent conjunctiva erosion. The GDD 2 can have a smooth profile and smooth edges to prevent injury and scarring.

The smaller tube 6 diameter can minimize the risk of damaging the cornea during insertion of the tube 6 into the eye and/or when the tube 6 is retained in the eye. Thus, the smaller tube 6 size and/or diameter can aid in preventing cornea decompensation and/or cornea damage.

The smaller tube 6 size and/or diameter can create a lower profile on the conjunctiva that can minimize tube 6 erosion.

A pre-cut, pre-bevelled tube 6 can provide an atraumatic profile that can prevent damage to the eye during insertion and/or when retained in the eye.

The length of the tube 6 of the GDD 2 can be readily adjusted and customized without having to remove the tube 6 from the eye and without having to perform a re-insertion of the tube 6 into the eye. As a result, possible trauma to the anterior chamber angle and the iris can therefore be prevented. Also, as a result, possible bleeding in the anterior chamber angle and the iris can be prevented. Further, because the adjustable tube 6 of the present disclosure negates the need to remove the tube from the eye, customize the length of the tube, and reinsert the tube in the eye, possible enlargement of the tunnel through which the tube 6 is inserted is prevented thereby reducing the associated risk of peri-tube leakage and/or hypotony.

One or more micro-holes 38 in the tube 6 can ensure continued functioning of the GDD 2. The one or more micro-holes 38 in the tube 6 can provide an outflow in the event that the tip of the tube 6 becomes occluded. Thus, the one or more micro-holes 38 along the length of the tube 6 can prevent occlusion.

The cuff 18 functioning as a flow restrictor on the GDD 2 and/or the stability system (e.g., the plate 4 plus the material comprising collagen and/or the viscoelastic substance) for controlling the fluid flow in the GDD 2 can aid in preventing early stage hypotony and/or late stage raised IOP. Early stage hypotony and late stage raised IOP are commonly associated with poor fluid flow control.

The material comprising collagen (e.g., pericardium, pericardial tissue and/or donor sclera) can brace the conjunctiva and can minimize artificial stretching and/or thickening. Thus, the material comprising collagen can minimize and/or prevent scarring. The material comprising collagen can also minimize the occurrence and/or severity of the raised IOP phase.

The viscoelastic substance (e.g., sodium hyaluronate and/or a cross-linked hyaluronic acid) can lift and expand the conjunctiva to prevent scarring and associated poor bleb formation.

In some embodiments, the GDD 2, plate 4 and/or tube 6 can be used for treating a mammal(s). In some embodiments, the mammal can be a human. In some embodiments, the human can be an adult. In some embodiments, the human can be a child.

Application

In a non-limiting exemplary application, the glaucoma drainage device of the present disclosure can be used for decreasing intra-ocular pressure (IOP) in glaucoma patients.

While various aspects and embodiments have been disclosed herein, it will be apparent that various other modifications and adaptations of the invention will be apparent to the person skilled in the art after reading the foregoing disclosure without departing from the spirit and scope of the invention and it is intended that all such modifications and adaptations come within the scope of the appended claims. The various aspects and embodiments disclosed herein are for purposes of illustration and are not intended to be limiting, with the true scope of the invention being indicated by the appended claims.

The invention claimed is:

1. An implantable ocular device comprising:
   a plate, wherein the plate comprises:
   a material; and
   a tube retaining structure integrally formed with the plate, wherein the tube retaining structure is configured to hold a tube retained by the tube retaining structure to the plate when the tube is displaced relative to the tube retaining structure;

a first layer comprising collagen adapted to cover at least a portion of the plate; and a second layer comprising a viscoelastic substance adapted to cover at least a portion of the first layer, wherein the first and second layers are adapted to control a fluid flow from a patient's eye.

2. The implantable ocular device of claim 1, wherein the tube retaining structure comprises at least one of a low profile ridge and a tube receiving channel having a horseshoe shape.

3. The implantable ocular device of claim 1, wherein the plate further comprises:
at least one plate channel; and
a reservoir,
wherein the plate channel runs from the tube retaining structure to the reservoir and to one or more ends of the plate.

4. The implantable ocular device of claim 3, wherein the at least one plate channel is undercut with respect to an exterior surface of the plate, and wherein the at least one plate channel comprises a diameter that corresponds with an outer diameter of the tube.

5. The implantable ocular device of claim 3, wherein the first layer is adapted to cover at least a portion of a top surface of the plate and/or at least a portion of the reservoir.

6. The implantable ocular device of claim 1, wherein the second layer is adapted to brace and/or to lift and expand the conjunctiva of the patient's eye.

7. The implantable ocular device of claim 1, wherein the first layer further comprises elastin and wherein the viscoelastic substance is selected from the group consisting of sodium hyaluronate, cross-linked hyaluronic acid or a combination thereof.

8. The implantable ocular device of claim 1, wherein the second layer is injectable over the first layer, and wherein the second layer is adapted to be applied around the plate.

9. The implantable ocular device of claim 1, wherein the plate further comprises at least one hole.

10. The implantable ocular device of claim 1, further comprising a tube comprising a length and having a proximal end and a distal end and wherein the tube further comprises one or more micro-holes having an inner diameter approximately equal to the inner diameter of the tube, and wherein the distal end of the tube is optionally bevelled.

11. The implantable ocular device of claim 10, wherein the tube further comprises a biodegradable cuff comprising a length that conforms to the curvature of an eye, the biodegradable cuff further comprising a diameter that causes an inner diameter of the tube to be narrowed, wherein the narrowed inner diameter of the tube allows a fluid flow rate of 2 µL/min or less through the tube.

12. The implantable ocular device of claim 11, wherein the biodegradable cuff begins to degrade between 4 weeks after implantation and 8 weeks after implantation.

13. A method of manufacturing or implanting an implantable ocular device, the method comprising:
providing and moulding a medical grade elastomer material for manufacturing a plate of the implantable ocular device, wherein the plate comprises:
a material; and
a tube retaining structure integrally formed with the plate;
covering at least a portion of the plate with a first layer comprising collagen;
covering at least a portion of the first layer with a second layer comprising a viscoelastic substance, and
wherein the tube retaining structure is configured to secure a tube to the plate when the tube is displaced relative to the tube retaining structure, and wherein the first and second layers are adapted to control a fluid flow from a patient's eye.

14. The method of claim 13, wherein the step of covering at least a portion of the first layer with the second layer comprises injecting the second layer over the first layer.

15. The method of claim 13, further comprising the step of applying the second layer around the plate.

16. The method of claim 13, further comprising at least one of polishing the moulded medical grade elastomer material; threading the tube through a tube receiving hole of the plate; and over-moulding the plate onto the tube.

17. The method of claim 13, further comprising:
forming in an eye a sub-Tenon's/subconjunctival pocket having a size corresponding to a size of the plate;
placing the plate over a sclera of the eye in the subconjunctival pocket and securing the plate with sutures; and
inserting a distal end of the tube into an anterior chamber of the eye.

18. The method of claim 13, wherein excess fluid is drained out from the anterior chamber via the tube and dissipated through the plate thereby reducing excess intraocular pressure (TOP).

19. The method of claim 13, further comprising adjusting a length of the tube by moving the tube away or toward a tube receiving hole corresponding to the tube retaining structure without the distal end of the tube being removed from the anterior chamber of the eye and with the tube being secured in the tube retaining structure.

20. The method of claim 13, further comprising cutting an excess tube length from the proximal end of the tube extending away from the tube receiving hole while the tube remains secured in the tube retaining structure.

* * * * *